United States Patent
Apley et al.

(10) Patent No.: US 12,150,974 B2
(45) Date of Patent: Nov. 26, 2024

(54) CONJUGATES WITH INHIBITORY RECEPTOR LIGANDS TO INDUCE ANERGY IN INSULIN-BINDING B CELLS

(71) Applicant: University of Kansas, Lawrence, KS (US)

(72) Inventors: Kyle Apley, Olathe, KS (US); Mark Farrell, Lawrence, KS (US); Cory Berkland, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 18/274,166

(22) PCT Filed: Jan. 27, 2022

(86) PCT No.: PCT/US2022/014070
§ 371 (c)(1),
(2) Date: Jul. 25, 2023

(87) PCT Pub. No.: WO2022/165016
PCT Pub. Date: Aug. 4, 2022

(65) Prior Publication Data
US 2024/0269239 A1    Aug. 15, 2024

Related U.S. Application Data

(60) Provisional application No. 63/142,224, filed on Jan. 27, 2021.

(51) Int. Cl.
| | |
|---|---|
| *A61K 38/28* | (2006.01) |
| *A61K 38/48* | (2006.01) |
| *A61K 39/00* | (2006.01) |
| *A61K 47/54* | (2017.01) |
| *A61K 47/60* | (2017.01) |
| *A61P 3/10* | (2006.01) |
| *C07D 249/04* | (2006.01) |
| *C07H 15/26* | (2006.01) |
| *C07K 14/62* | (2006.01) |

(52) U.S. Cl.
CPC .............. *A61K 38/28* (2013.01); *A61K 38/48* (2013.01); *A61K 39/0008* (2013.01); *A61K 47/545* (2017.08); *A61K 47/549* (2017.08); *A61K 47/60* (2017.08); *A61P 3/10* (2018.01); *C07D 249/04* (2013.01); *C07H 15/26* (2013.01); *C07K 14/62* (2013.01)

(58) Field of Classification Search
None
See application file for complete search history.

(56) References Cited

U.S. PATENT DOCUMENTS

| | | |
|---|---|---|
| 2013/0018187 A1 | 1/2013 | Konradi et al. |
| 2013/0116407 A1 | 5/2013 | Ashley et al. |
| 2013/0189519 A1 | 7/2013 | Forrest et al. |
| 2018/0297981 A1 | 10/2018 | Jacobson et al. |

OTHER PUBLICATIONS

Ferreira et al. "Disulfide bond disrupting agents activate the unfolded protein response in EGFR- and HER2-positive breast tumor cells", Oncotarget, vol. 8, No. 17, Mar. 7, 2017, pp. 28971-28989, Retrieved from the Internet: <URL:https://www.ncbi.nlm.nlh.gov/pmc/articles/PMC5438706/>.

International Search Report & Written Opinion of the International Searching Authority issued in International Application No. PCT/US2022/014070 mailed May 4, 2022, 8 pages.

*Primary Examiner* — Dale R Miller
(74) *Attorney, Agent, or Firm* — Foley & Lardner LLP

(57) ABSTRACT

The present disclosure provides conjugates, methods of making the same, and uses thereof. The conjugates of the present technology are useful in inducing anergy in insulin-binding B cells.

20 Claims, 17 Drawing Sheets

Specification includes a Sequence Listing.

A)

B)

C)

| Species | EC$_{50}$ (uM) | Fold Increase |
|---|---|---|
| Insulin (Zn free) | 0.003 | |
| Desoctapeptide Insulin | 108 | 36559 |
| Insulin(F25D)-LPETGGHG | 24 | 7962 |
| Proinsulin(PI)-LPTEGGHG | 0.71 | 240 |
| Proinsulin(F25D)-LPETGGHG | > 100 | >40000 |
| Proinsulin(F25D, Y19A)-LPETGGHG | 33 | 11143 |
| Proinsulin(F25D, Lispro)-LPETGGHG | > 100 | >40000 |
| Proinsulin(F25D, DKP)-LPETGGHG | 52 | 17458 |

| Species | Minima (nM) | % Alpha-helical character |
|---|---|---|
| Insulin | 208.0 | 39.3 |
| Proinsulin-LPETGGHG | 206.5 | 16.5 |
| Proinsulin(F25D)-LPETGGHG | 205.5 | 14.3 |
| Proinsulin(F25D,Lispro)-LPETGGHG | 205.5 | 11.8 |
| Proinsulin(F25D,DKP)-LPETGGHG | 205.5 | 7.0 |
| 4-arm PEG-alkyne (20K) | - | 0.0 |
| 4-arm PEG-insulin(4) | 207.5 | 30.0 |
| 4-arm PEG-proinsulin(F25D) | 205.5 | 11.8 |
| 4-arm PEG-Proinsulin(F25D, Lispro) | 205.0 | 4.2 |
| 4-arm PEG-Proinsulin(F25D, DKP) | 204.5 | 5.1 |

CONJUGATES WITH INHIBITORY RECEPTOR LIGANDS TO INDUCE ANERGY IN INSULIN-BINDING B CELLS

CROSS-REFERENCE TO RELATED APPLICATIONS

This application is a U.S. National Stage Application under 35 U.S.C. § 371 of International Patent Application No. PCT/US2022/014070, filed Jan. 27, 2022, which claims the benefit of and priority to U.S. Provisional Patent Application No. 63/142,224, filed Jan. 27, 2021, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 1, 2022, is named 104434-0276_SL.txt and is 8,113 bytes in size.

TECHNICAL FIELD

The present technology relates generally to conjugates, methods of making the same, and uses thereof. The conjugates of the present technology are useful in inducing anergy in insulin-binding B cells.

BACKGROUND

The following description of the background of the present technology is provided simply as an aid in understanding the present technology and is not admitted to describe or constitute prior art to the present technology.

Type 1 Diabetes (T1D) is an autoimmune disease caused by the loss of self-tolerance for islet antigens and subsequent T cell-mediated destruction of the pancreatic islets, including the beta cells responsible for producing insulin and regulating blood glucose. Self-tolerance is the ability of the immune system to recognize but not respond in an inflammatory manner to self-tissue and is coordinated both centrally and peripherally. Failures in central tolerance in T1D are indicated by the genetic risk factors for certain human leukocyte antigen (HLA) alleles that encode the major histocompatibility complex class II (MHC II). These alleles allow the MHC II to weakly bind the T cell epitope of insulin, the key antigen, and enable some insulin-reactive T cells to evade negative selection and clonal deletion within central tolerance. Once in the periphery, the autoreactive T cells can be activated to mount an immune response against insulin and attack the beta cells (Stadinski, B. D. et al., *Proceedings of the National Academy of Sciences* 2010, 107 (24), 10978).

Failure to maintain peripheral tolerance has also been indicated in T1D pathogenesis. While T1D is T cell-mediated, antigen presenting cells (APCs), such as B cells, play a role in disease onset through T cell activation (Creusot, R. J. et al., *Diabetes* 2018, 67 (8), 1481). Self-reactive B cells exist in the periphery yet help maintain peripheral tolerance by persisting in an anergic, or unreactive, state. A transient reduction in insulin-binding anergic B cells has been correlated with the onset of T1D and suggests that the loss of anergic B cells contributes to the activation of autoreactive T cells and the onset of disease (Smith, M. J. et al., *Diabetes* 2015, 64 (5), 1703). Conservation of peripheral tolerance through B cell anergy has been proposed as a prophylactic treatment for individuals at a high risk of developing T1D.

Thus, there is a need for treatments and prophylaxes for autoimmune diseases such as T1D that avoid adverse effects caused by the destruction of healthy cells.

SUMMARY OF THE PRESENT TECHNOLOGY

In an aspect, the present disclosure provides a conjugate of Formula I

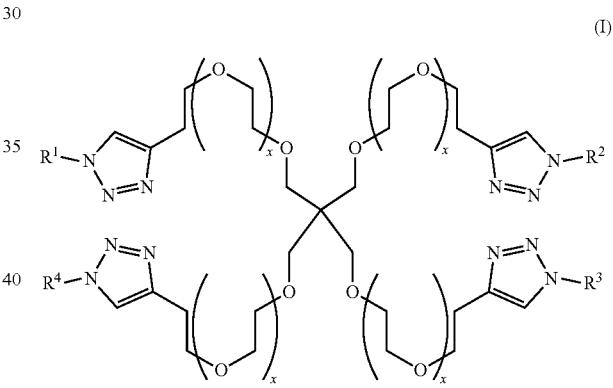

(I)

or a pharmaceutically acceptable salt and/or solvate thereof, wherein $R^1$, $R^2$, $R^3$, and $R^4$ are each independently

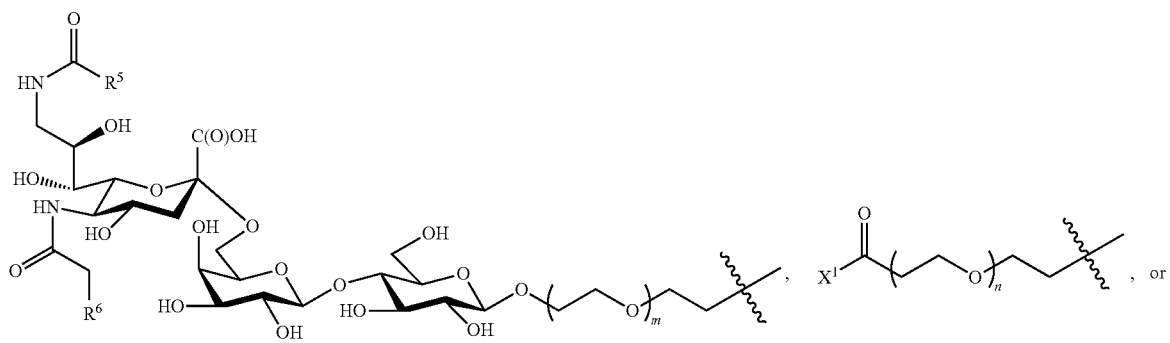

$$X^2 \diagdown \underset{H}{\overset{H}{N}} \diagdown \diagdown \diagdown O \diagdown_p \diagdown \diagdown \diagdown \xi \, ;$$

R⁵ is independently at each occurrence aryl or aralkyl;

R⁶ is independently at each occurrence halo, hydroxyl, aryl, or heteroaryl;

X¹ is independently at each occurrence a F-nitrogen atom of lysine of SEQ ID NO: 2 or a substitution variant thereof of a first proinsulin polypeptide;

X² is independently at each occurrence a carbonyl carbon of a nitrogen atom of a C-terminal glycine of a sortase moiety wherein the sortase moiety is fused to a second proinsulin polypeptide a C-terminus of the second proinsulin polypeptide;

x is independently at each occurrence 0, 1, 2, 3, 4, 5, 6, 7, 8, 9, 10, 11, or 12;

m is independently at each occurrence 0, 1, 2, 3, 4, 5, 6, 7, 8, 9, 10, 11, or 12;

n is independently at each occurrence 0, 1, 2, 3, 4, 5, 6, 7, 8, 9, 10, 11, or 12; and p is independently at each occurrence 0, 1, 2, 3, 4, 5, 6, 7, 8, 9, 10, 11, or 12.

In an aspect, the present disclosure provides a composition that includes a conjugate of any embodiment disclosed herein as well as a pharmaceutically acceptable carrier or one or more excipients, fillers or agents (collectively referred to hereafter as "pharmaceutically acceptable carrier" unless otherwise indicated and/or specified).

In a related aspect, a medicament for treating or preventing autoimmune diabetes in a subject is provided, where the medicament includes a conjugate of any embodiment disclosed herein and optionally a pharmaceutically acceptable carrier.

In a related aspect, a pharmaceutical composition is provided that includes a pharmaceutically acceptable carrier and an effective amount of a conjugate of any embodiment disclosed herein.

In an aspect, a method for treating or preventing autoimmune diabetes in a subject in need thereof is provided, where the method includes administering to the subject an effective amount of the conjugate of any embodiment disclosed herein.

BRIEF DESCRIPTION OF THE DRAWINGS

FIG. 2A discloses SEQ ID NO: 13.

FIGS. 3A-3B depict the primary, secondary, and tertiary structures and sequences of human insulin and the proinsulin variants. Mutations and alterations to human insulin and proinsulin are noted along with the residues involved in hormonal insulin receptor binding (IR-B), T cell epitopes, and key B cell epitopes. B cell epitope includes amino acid residue 3 of the insulin B-chain and amino acid residues 4 and 8-10 of the insulin A-chain. T cell epitopes include amino acid residues 9-23 of the insulin B-chain and each residue of a C-peptide fragment having QVELGGGPGAGSLQPLALEGSLQKR (SEQ ID NO: 7). The proinsulin variant comprises the substitutions F25D in the insulin B-chain, and Y19A in the insulin A-chain, which reduce insulin receptor (IR) affinity. The proinsulin variant may further comprise the substitutions P28K and K29P (Lispro), or P28K, K29P and H10D (DKP) in the insulin B-chain, which reduce self-association. The sequence of the sortase tag is LPETGGHG (SEQ ID NO: 6). Native proinsulin excludes the red eSrtA tags and the F25D mutation. Insulin does not contain the C-peptide. FIG. 3A discloses SEQ ID NOS 4 and 2, respectively, in order of appearance. FIG. 3B discloses SEQ ID NO: 14.

FIG. 4A: SDS-PAGE gel of a standard ladder (lane 1) purified $G_3$-proinsulin at low and high concentrations (lanes 2, 4) and of the unpurified fusion-precursor FP-$G_3$-proinsulin at low and high concentrations (lanes 3, 5). FIG. 4B: HPLC chromatogram of purified $G_3$-proinsulin on a Waters reverse-phase BEH C4 column with a 27_40% ACN 20-minute gradient. The major peak accounts for >90% AUC. FIG. 4C: Mass spectrum from LC-ESI-TOF mass spectrometer. The major peak at 9559.7 m/z matches the calculated mass for the [M+H]⁺ ion of $G_3$-proinsulin.

FIG. 5A: Synthesis of alkyne-PEG$_n$-$G_3$Proinsulin where n=10 kDa or 20 kDa. FIG. 5A discloses SEQ ID NOS 6, 13 and 13, respectively, in order of appearance. FIG. 5B: Synthesis of Alkyne-$G_3$Proinsulin. FIG. 5B discloses SEQ ID NOS 6 and 13, respectively, in order of appearance. FIG. 5C: Synthesis of alkyne-PEG$_n$-(proinsulinLPETG ("LPETG" disclosed as SEQ ID NO: 11)) where n=10 kDa or 20 kDa. FIG. 5C discloses SEQ ID NOS 6, 13, 11, 11, 13 and 11, respectively, in order of appearance.

FIG. 6A: Structure of the azide-functionalized high affinity, high specificity CD22 ligand. FIG. 6B: Synthesis of CD22L-$G_3$Proinsulin. FIG. 6B discloses SEQ ID NO: 13. FIG. 6C: Synthesis of CD22L-PEG$_n$-$G_3$Proinsulin where n=10 kDa or 20 kDa. Alternatively, CD22L-PEG$_n$-(ProinsulinLPETG ("LPETG" disclosed as SEQ ID NO: 11)) can be prepared in an analogous manner by replacing Alkyne-PEG$_n$-$G_3$Proinsulin with Alkyne-PEG$_n$-(ProinsulinLPETG ("LPETG" disclosed as SEQ ID NO: 11)). FIG. 6C discloses SEQ ID NO: 13.

FIG. 7 discloses SEQ ID NOS 6, 15, 6, 6, 6 and 6, respectively, in order of appearance.

FIG. 8 discloses SEQ ID NOS 11, 6, 15, 6, 6, 6 and 6, respectively, in order of appearance.

FIG. 9 discloses "LPETGGHG" as SEQ ID NO: 6.

FIG. 12 discloses "LPETGGHG" as SEQ ID NO: 6.

FIG. 13 discloses "LPETGGHG" as SEQ ID NO: 6.

FIG. 15 discloses "LPETGGG" as SEQ ID NO: 13.

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) Weir's *Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Figure 3A:
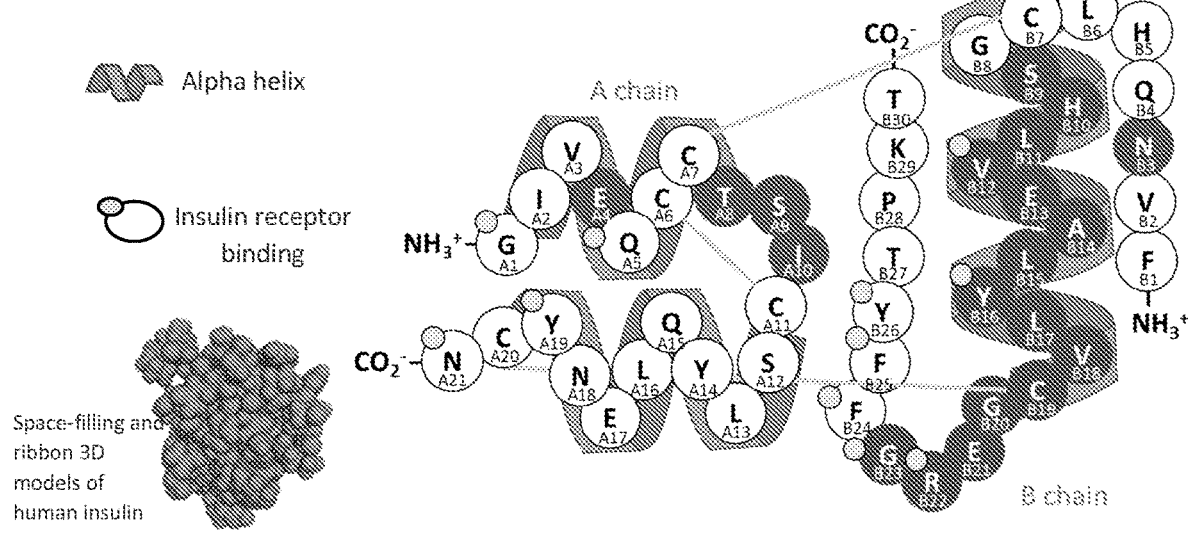
FIGS. 3A-3B show human insulin and human proinsulin variants, respectively.
Figure 3B:
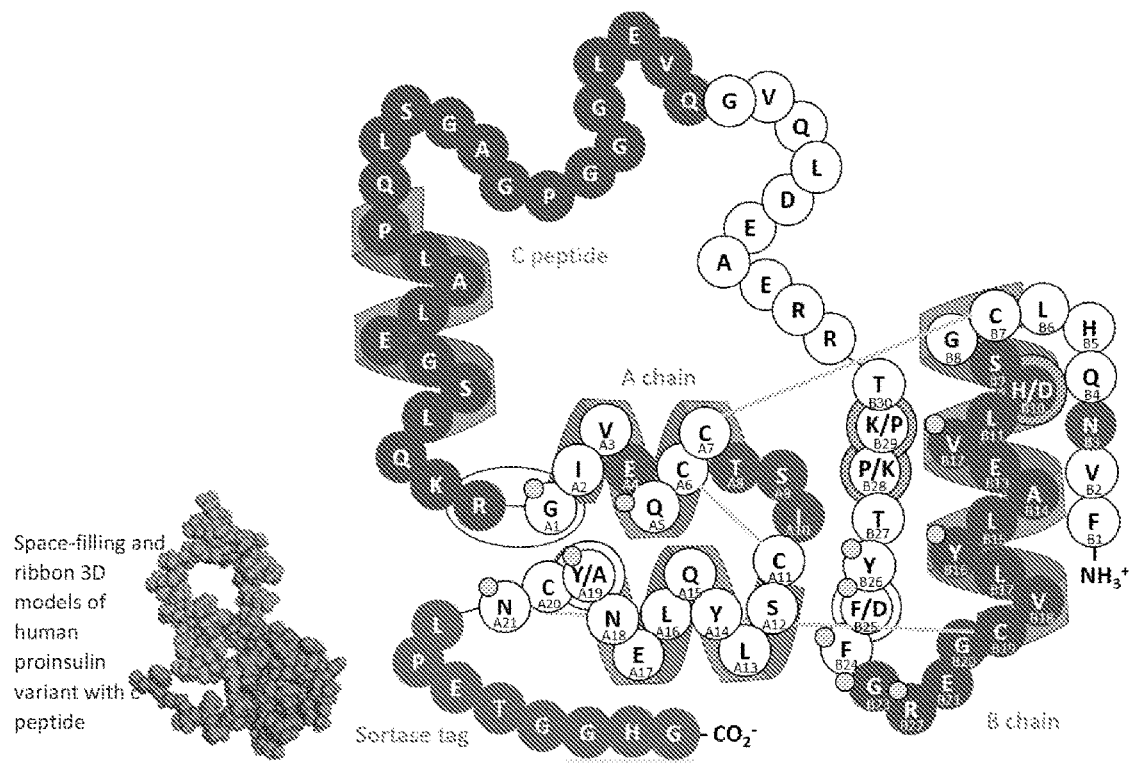

Without wishing to be bound by theory, it is believed that it is important to reduce the hormonal activity of proinsulin to minimize risk of hypoglycemia while maintaining its epitopes to be recognized by immune receptors. Insulin receptor B is responsible for metabolic regulation and has affinity for proinsulin 20-30 fold less than insulin (Malaguarnera, R. et al., *Endocrinology* 2012, 153, 2152-2163; Belfiore, A. et al., *Endocrine Reviews* 2017, 38, 379-431). As evident from FIGS. 3A-3B, the apparent co-dependence of immune and hormone recognition on similar regions presents a challenge in selectively reducing hormone function without adversely effecting epitope recognition.

The conjugates of the present technology show reduced hormone function, while maintaining binding kinetics and affinities (<10 nM) to anti-insulin antibodies that were comparable to native human insulin. Accordingly, the conjugates disclosed herein are useful in methods for inducing anergy in insulin-binding B cells and/or for the prevention and/or treatment of an autoimmune disease (e.g., autoimmune diabetes, e.g., Type 1 diabetes).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, $IC_{50}$ refers to the concentration of a conjugate at which a given biological function or biochemical process (e.g., binding to or inducing anergy in insulin-specific B cells) is inhibited by half.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

The phrase "and/or" as used in the present disclosure will be understood to mean any one of the recited members individually or a combination of any two or more thereof—for example, "A, B, and/or C" would mean "A, B, C, A and B, A and C, B and C, or the combination of A, B, and C."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{15}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; and nitriles (i.e., CN).

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neo-pentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH₃), —CH=C(CH₃)₂, —C(CH₃)=CH₂, —C(CH₃)=CH(CH₃), —C(CH₂CH₃)=CH₂, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, and —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl,azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O⁻. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecular weight" (also known as "relative molar mass") is a dimensionless quantity but is converted to molar mass by multiplying by 1 gram/mole or by multiplying by 1 Da—for example, a compound with a weight-average molecular weight of 5,000 has a weight-average molar mass of 5,000 g/mol and a weight-average molar mass of 5,000 Da.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism, and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

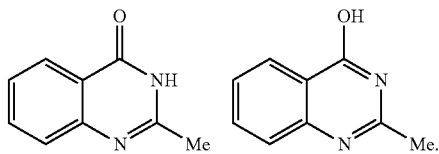

As another example, guanidines may exhibit the following isomeric forms in protic organic solution, also referred to as tautomers of each other:

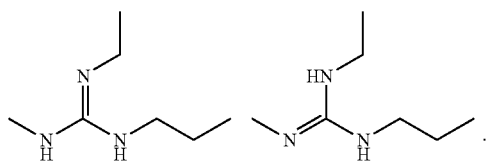

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, or topically. Administration includes self-administration and the administration by another.

As used herein, "anergy" refers to a lack of reaction by the body's defense mechanisms to foreign substances, and involves a direct induction of peripheral lymphocyte tolerance. An individual in a state of anergy often indicates that the immune system is unable to mount a normal immune response against a specific antigen, usually a self-antigen. Lymphocytes are said to be anergic when they fail to respond to their specific antigen. Anergy thus induces tolerance by modifying the immune system to prevent self-destruction.

As used herein, the term "autoantibody" refers to an antibody that targets and/or reacts with one or more of an individual's own proteins, cells, tissues, or organs. The term "autoantigen" as used herein refers to an antigen composed of normal tissue, cells, protein, peptides, or DNA that is the target of an immune response (e.g., a humoral or cell-mediated immune response). An autoantigen may be targeted by or react with an autoantibody in the case of an autoimmune disease.

As used herein, "autoimmune diabetes" refers to diabetes that is characterized by the destruction of the insulin-producing β-cells of the pancreas.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from eye, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a tissue sample obtained by needle biopsy.

As used herein, the term "cell surface receptor" refers to a molecule such as a protein, generally found on the external surface of a cell membrane and which interacts with soluble molecules, e.g., that circulate in the blood supply. Cell surface receptors may also be secreted in a soluble form into the extracellular space or may be shed from the external surface of a cell. In some embodiments, a cell surface receptor may include an antigen, or an antigen receptor. In other embodiments, B lymphocytes, also termed B cells, have cell surface receptors that are referred to as "B cell receptors", or "BCR", or in some cases "IgM" receptor.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein (e.g., autoimmune diabetes, e.g., Type 1 diabetes). As used herein, a "therapeutically effective amount" of a composition refers to composition levels in which the physiological effects of a disease or condition are ameliorated or eliminated. A therapeutically effective amount can be given in one or more administrations. As used herein, a "prophylactically effective amount" of a composition refers to composition levels that prevent or delay the onset of at least one symptom of a disease or condition described herein. A prophylactically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the terms "individual", "patient", or "subject" can be an individual organism, a vertebrate, a mammal, or a human. In some embodiments, the individual, patient or subject is a human.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20th edition, ed. A. Gennaro, 2000, Lippincott, Williams & Wilkins, Philadelphia, Pa.). Examples of pharmaceutically-acceptable carriers include a liquid or solid filler, diluent, excipient, manufacturing aid (e.g., lubricant, talc magnesium, calcium or zinc stearate, or steric acid), or solvent encapsulating material, useful for introducing the active agent into the body.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, preventing an autoimmune disease (e.g., autoimmune diabetes, e.g., Type 1 diabetes), includes preventing or delaying the initiation of symptoms of an autoimmune disease (e.g., autoimmune diabetes, e.g., Type 1 diabetes). As used herein, prevention of an autoimmune disease (e.g., autoimmune diabetes, e.g., Type 1 diabetes) also includes preventing a recurrence of one or more signs or symptoms of an autoimmune disease (e.g., autoimmune diabetes, e.g., Type 1 diabetes).

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Insulin

Insulin is a peptide hormone produced by β-cells in the islets of Langerhans within the pancreas. Insulin functions by regulating the absorption of glucose from the blood. When exposed to a stimulus, such as increased protein and glucose levels, insulin is released from 3-cells and binds to the insulin receptor, initiating a signaling cascade that affects many aspects of human metabolism. Disruption of this process is directly related to several diseases, autoimmune diabetes (e.g., Type 1 diabetes), insulinoma, insulin resistance, metabolic syndromes, and polycystic ovary syndrome. The amino acid sequence of insulin is strongly conserved throughout evolution, particularly in vertebrates, and consists of two polypeptide chains, termed the A and B chains, that are linked through disulfide bonds.

Insulin is initially synthesized as an inactive precursor called preproinuslin. Through a series of highly coordinated, enzyme-regulated steps, preproinsulin is converted into mature insulin. Cleavage of the signal peptide of preproinsulin in the endoplasmic reticulum followed by oxidation and chaperone-assisted folding yields proinsulin, which is transported to the trans-Golgi network. Proinsulin is then subjected to further proteolytic processing steps, resulting in the release of a fragment called the C-peptide and formation of mature insulin, which is stored within zinc ($Zn^{2+}$) and calcium ($Ca^{2+}$)-rich secretory vesicles in j-cells as an inactive hexamer. After exposure to a stimulus, the secretory vesicles fuse with the plasma membrane, releasing the insulin and promoting the dissociation of the hexamers into active insulin monomers.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology.

Type 1 Diabetes

Lifetime insulin-replacement therapy is the current treatment for T1D and requires consistent blood glucose monitoring. Unfortunately, this approach cannot perfectly regulate blood glucose and results in chronic hyperglycemia that increases the risk for kidney, nerve, and heart disease. A large clinical trial demonstrated that intensive blood glucose regulation practices that minimize chronic hyperglycemia reduced the risk for these co-morbidities (Group, T. D. C. a. C. T. R., *New England Journal of Medicine* 1993, 329 (14), 977-986). Therefore, a treatment that can retain or regain residual beta cell function to aid in blood glucose regulation should improve patient outcomes.

Immunotherapies have been evaluated in T1D clinical trials with the goal of retaining or regaining beta cell function. The ideal immunotherapy for T1D will be antigen-specific to anergize or delete the autoreactive B and T cells without lowering defenses against infections. Maintaining defenses against infection is especially relevant for T1D as the disease primarily starts in children and insulin-replacement therapy is relatively safe. Therefore, therapies that rely on global immune suppression will carry higher levels of risk, especially if they require chronic administration. Unfortunately, the most practical antigen-specific approach, antigen administration at mucosal surfaces, failed to induce sufficient tolerance to preserve beta cell function in numerous clinical trials (Jacobsen, L. M et al., *Current Diabetes Reports* 2018, 18 (10), 90). Therefore, investigating new approaches to restore tolerance in an antigen-specific manner is warranted.

While not the ideal treatment, many globally immunosuppressive therapies have been investigated in clinical trials and offer insight into potential targets for antigen-specific approaches. The B cell-deleting anti-CD20 antibody rituximab demonstrated beta cell preservation with increased endogenous insulin production, reduced exogenous insulin need, and reduced hemoglobin A1C at 1 year (Bluestone, J. A. et al. *Nature* 2010, 464 (7293), 1293-1300). This outcome is hypothesized to result from the loss of autoreactive B cells that promote disease by either secreting inflammatory cytokines in the pancreas or presenting autoantigen to T cells.

Conjugates of the Present Technology

The conjugates of the present technology are based on the premise that B cells actively contribute to T1D and therefore may be targeted to induce antigen-specific tolerance.

Figure 1:
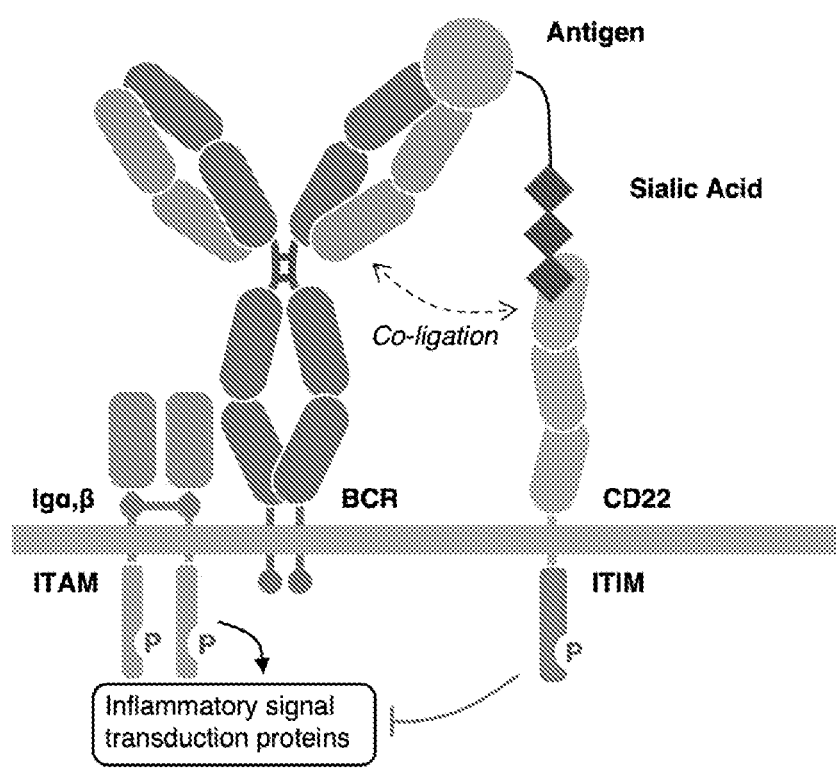
FIG. 1: B cell activation signaling is invoked by antigen binding to the B cell receptor (BCR) and phosphorylation of the immunoreceptor tyrosine-based activation motif (ITAM). The B cell activation inhibitory signaling pathways can be invoked by co-ligation of the BCR with binding of alpha2,6-linked sialic acid to CD22. This inhibitory signaling pathways block B cell activation by dephosphorylating inflammatory signal transduction proteins.

The antigen specificity of B cells is determined by the membrane-immobilized, antibody-like B cell receptor (BCR). A unique receptor has been identified on B cells that, when co-localized with the BCR, shuts down the inflammatory signaling pathway and promotes B cell anergy (FIG. 1). This immune-response inhibitory receptor is CD22, a sialic acid-binding Ig-like lectin (siglec) receptor with binding preference for alpha2,6-linked sialylated glycans. This receptor has been implicated to function as a self vs. non-self recognition mechanism as many mammalian proteins possess sialic acid terminated glycans unlike bacterial and yeast proteins. The inflammation inhibitory response from CD22 is generated by its intracellular immunoreceptor tyrosine-based inhibitory motif (ITIM). Binding of both BCR and CD22 with multivalent polymers displaying dinitrophenol (DNP) and high-affinity CD22 ligands was shown to prevent increased calcium flux, reduce phosphorylation of immune activating response pathway proteins, and stimulate endocytosis of the BCR in a DNP-specific B cell line and in mice.

Proinsulin variants. Native proinsulin comprises an insulin B-chain, an insulin C-chain, and an insulin A-chain. By way of example, the complete amino acid sequence of native human proinsulin is FVNQHLCGSHLVEALYL-VCGERGFFYTPKTRREAEDLQVGQVELGGGP-GAGSLQPL ALEGSLQKRGIVEQCCTSICSLYQLE-NYCN (SEQ ID NO: 1)

The native amino acid sequences of each of these chains is provided below:

Insulin B-chain: FVNQHLCGSHLVEALYL-VCGERGFFYTPKT (SEQ ID NO: 2)

Insulin C-chain: RREAEDLQVGQVELGGGP-GAGSLQPLALEGSLQKR (SEQ ID NO: 3)

Insulin A-chain: GIVEQCCTSICSLYQLENYCN (SEQ ID NO: 4)

In an aspect, the present disclosure provides a conjugate of Formula I

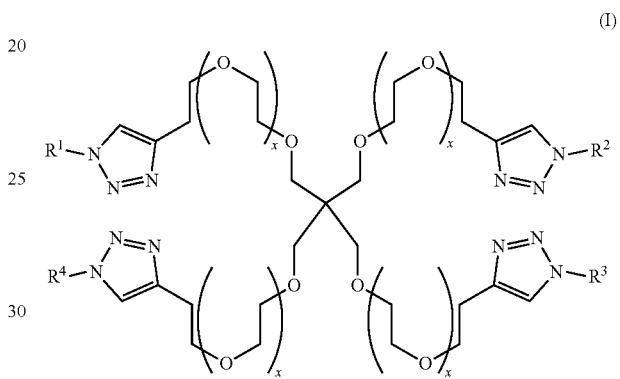

or a pharmaceutically acceptable salt and/or solvate thereof, wherein $R^1$, $R^2$, $R^3$, and $R^4$ are each independently

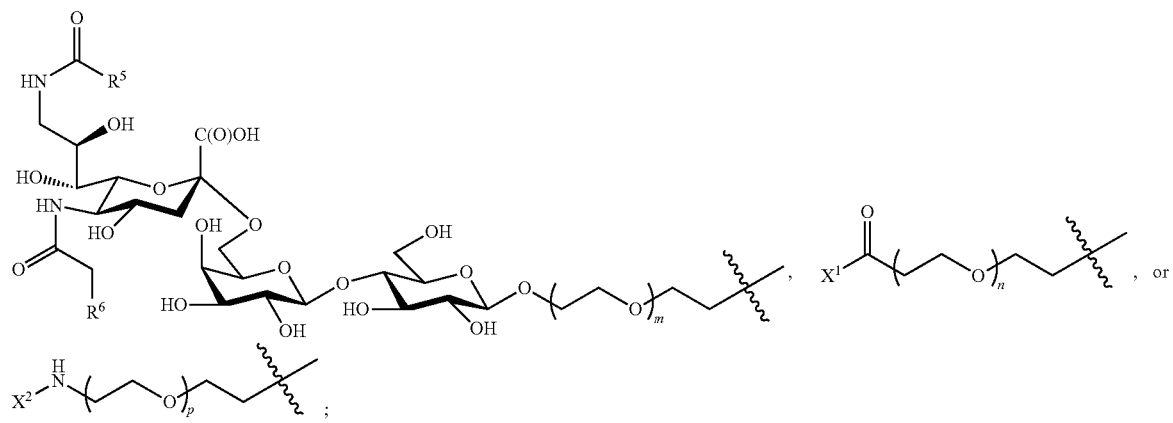

$R^5$ is independently at each occurrence aryl or aralkyl;

$R^6$ is independently at each occurrence halo, hydroxyl, aryl, or heteroaryl;

$X^1$ is independently at each occurrence a F-nitrogen atom of lysine of SEQ ID NO: 2 or a substitution variant thereof of a first proinsulin polypeptide;

$X^2$ is independently at each occurrence a carbonyl carbon of a nitrogen atom of a C-terminal glycine of a sortase moiety wherein the sortase moiety is fused to a second proinsulin polypeptide a C-terminus of the second proinsulin polypeptide;

x is independently at each occurrence 0, 1, 2, 3, 4, 5, 6, 7, 8, 9, 10, 11, or 12;

m is independently at each occurrence 0, 1, 2, 3, 4, 5, 6, 7, 8, 9, 10, 11, or 12;

n is independently at each occurrence 0, 1, 2, 3, 4, 5, 6, 7, 8, 9, 10, 11, or 12; and p is independently at each occurrence 0, 1, 2, 3, 4, 5, 6, 7, 8, 9, 10, 11, or 12.

For the sake of clarity, a representation of the amino acid L-lysine is provided below indicating the F-nitrogen atom.

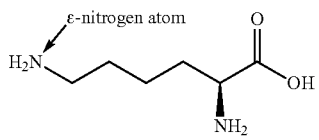

The conjugates of the present technology may include a proinsulin polypeptide that is fused to a sortase moiety, wherein the proinsulin polypeptide includes an insulin B-chain, an insulin C-chain, and an insulin A-chain. The sortase moiety may be located at the N-terminus or the C-terminus of the proinsulin polypeptide. Additionally or alternatively, in some embodiments of the conjugates disclosed herein, the sequence of the sortase moiety is LPETGGHG (SEQ ID NO: 6).

Additionally or alternatively, in some embodiments of the conjugates disclosed herein, the proinsulin polypeptide comprises a F25D substitution in the insulin B-chain (SEQ ID NO: 2) and/or a Y19A or Y19L substitution in the insulin A-chain (SEQ ID NO: 4).

Additionally or alternatively, in some embodiments of the conjugates disclosed herein, the proinsulin polypeptide includes a H10D substitution in the insulin B-chain (SEQ ID NO: 2). Additionally or alternatively, in certain embodiments of the conjugates disclosed herein, the proinsulin polypeptide includes both P28K and K29P substitutions in the insulin B-chain (SEQ ID NO: 2). In some embodiments of the conjugates disclosed herein, the proinsulin polypeptide includes P28K, K29P and H10D substitutions in the insulin B-chain (SEQ ID NO: 2). The proinsulin polypeptide may or may not include a signal peptide sequence. The signal peptide sequence may be a native or engineered signal peptide sequence. In certain embodiments, the signal peptide sequence is MGSSHHHHHHSSFLDPVLM (SEQ ID NO: 5).

Additionally or alternatively, in some embodiments of the conjugates disclosed herein, the proinsulin polypeptide comprises an amino acid sequence selected from among
native proinsulin sequence (beta, C-, alpha peptide) (SEQ ID NO: 8)
MGSSHHHHIH SSFLDPVLMF VNQHLCGSHL VEALYLVCGE RGFFYTPKTR REAEDLQVGQ VELGGGPGAG SLQPLALEGS LQKRGIVEQC CTSICSLYQL ENYCN X38 (B25-Asp) proinsulin (beta, C-, alpha peptide, position variant bolded) (SEQ ID NO: 9)
MGSSHHHIH SSFLDPVLMF VNQHLCGSHL VEALYLVCGE RGFDYTPKTR REAEDLQVGQ VELGGGPGAG SLQPLALEGS LQKRGIVEQC CTSICSLYQL ENYCN A19-Leu proinsulin (beta, C-, alpha peptide, position variant bolded) (SEQ ID NO: 10)
MGSSHHIHIHH SSFLDPVLMF VNQHLCGSHL VEALYLVCGE RGFFYTPKTR REAEDLQVGQ VELGGGPGAG SLQPLALEGS LQKRGIVEQC CTSICSLYQL ENLCN Additionally or alternatively, in some embodiments of the conjugates disclosed herein, the proinsulin polypeptide exhibits reduced activation of hormonal insulin receptor (IR) relative to native human insulin.

In any embodiment disclosed herein, it may be that the first proinsulin polypeptide is fused to a sortase moiety, wherein the first proinsulin polypeptide includes an insulin B-chain of SEQ ID NO: 2, an insulin C-chain of SEQ ID NO: 3, and an insulin A-chain of SEQ ID NO:4. In any embodiment disclosed herein, it may be that the sortase moiety is located at the N-terminus or the C-terminus of the first proinsulin polypeptide. In any embodiment disclosed herein, it may be that the sequence of the sortase moiety is SEQ ID NO: 6. In any embodiment disclosed herein, it may be that the first proinsulin polypeptide comprises a F25D substitution in the insulin B-chain of SEQ ID NO: 2 and/or a Y19A or Y19L substitution in an insulin A-chain of SEQ ID NO: 4. In any embodiment disclosed herein, it may be that the first proinsulin polypeptide comprises a H10D substitution in the insulin B-chain of SEQ ID NO: 2. In any embodiment disclosed herein, it may be that the first proinsulin polypeptide comprises both P28K and K29P substitutions in the insulin B-chain of SEQ ID NO: 2. In any embodiment disclosed herein, it may be that the first proinsulin polypeptide comprises P28K, K29P, and H10D substitutions in the insulin B-chain of SEQ ID NO: 2. In any embodiment disclosed herein, it may be that the first proinsulin polypeptide comprises a signal peptide sequence. In any embodiment disclosed herein, it may be that the signal peptide sequence is a native or engineered signal peptide sequence. In any embodiment disclosed herein, it may be that the signal peptide sequence is SEQ ID NO: 5.

In any embodiment disclosed herein, it may be that the second proinsulin polypeptide comprises a F25D substitution in an insulin B-chain of SEQ ID NO: 2 and/or a Y19A or Y19L substitution in an insulin A-chain of SEQ ID NO: 4. In any embodiment disclosed herein, it may be that the second proinsulin polypeptide comprises a H10D substitution in an insulin B-chain of SEQ ID NO: 2. In any embodiment disclosed herein, it may be that the second proinsulin polypeptide comprises both P28K and K29P substitutions in an insulin B-chain of SEQ ID NO: 2. In any embodiment disclosed herein, it may be that the second proinsulin polypeptide comprises P28K, K29P, and H10D substitutions in an insulin B-chain of SEQ ID NO: 2. In any embodiment disclosed herein, it may be that the second proinsulin polypeptide comprises a signal peptide sequence. In any embodiment disclosed herein, it may be that the signal peptide sequence is a native or engineered signal peptide sequence. In any embodiment disclosed herein, it may be that the signal peptide sequence is SEQ ID NO: 5. In any embodiment disclosed herein, it may be that the first proinsulin polypeptide and/or the second proinsulin polypeptide comprise an amino acid sequence selected from the group consisting of SEQ ID NOs: 8-10. In any embodiment disclosed herein, it may be that the first proinsulin polypeptide and the second proinsulin polypeptide are of the same sequence.

In any embodiment disclosed herein, the conjugate may have a volume-weighted average diameter as determined by dynamic light scattering of about 2 nm to about 15 nm. Thus, in any embodiment disclosed herein, the conjugate may have a volume-weighted average diameter as determined by dynamic light scattering of about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, or any range including and/or in between any two of these values. For example, in any embodiment disclosed herein, the conjugate may have a volume-weighted average diameter as determined by dynamic light scattering of about 4 nm to about 8 nm.

In any embodiment disclosed herein, the conjugate may have a number-average molecular weight of about 10,000 to about 150,000. Thus, in any embodiment disclosed herein, the conjugate may have a number-average molecular weight of about 10,000, about 20,000, about 30,000, about 40,000, about 50,000, about 60,000, about 70,000, about 80,000, about 90,000, about 100,000, about 110,000, about 120,000, about 130,000, about 140,000, about 150,000, or any range including and/or in between any two of these values. For example, in any embodiment disclosed herein, the conjugate may have a number-average molecular weight of about 40,000 to about 80,000.

As discussed above, $R^5$ is independently at each occurrence aryl or aralkyl and $R^6$ is independently at each occurrence halo, hydroxyl, aryl, or heteroaryl. See, e.g., Collins, B. E. et al. *J Immunol* 2006, 177, 2994-3003; Rillahan, C. D. et al. *Chem. Sci.* 2014, 5, 2398-2406; U.S. Pat. No. 9,981,023. In any embodiment disclosed herein, it may be that $R^6$ is independently at each occurrence halo or hydroxyl. In any embodiment disclosed herein, it may be that $R^5$ is independently at each occurrence

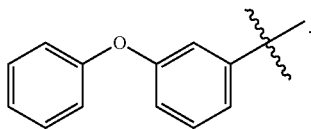 [SMILES: *c1cccc(Oc2ccccc2)c1]

or

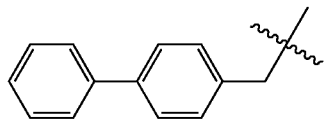 [SMILES: *Cc1ccc(-c2ccccc2)cc1]

Therapeutic and Prophylactic Methods of the Present Technology

The following discussion is presented by way of example only, and is not intended to be limiting.

Described herein are methods for treating or preventing an autoimmune disease (e.g., autoimmune diabetes, e.g., Type 1 diabetes) and/or inducing anergy in insulin-binding B cells, wherein the method comprises administering to a subject a conjugate described herein. In some embodiments of the methods disclosed herein, the autoimmune disease is autoimmune diabetes, e.g., diabetes mellitus type 1 (i.e., Type 1 diabetes (T1D), juvenile diabetes, or insulin-dependent diabetes), or latent autoimmune diabetes of adults (LADA). LADA, also referred to as slow onset Type 1 diabetes, is a form of diabetes mellitus type 1 that occurs in adults and presents with a slower course of onset. It is estimated that up to about 50% of adults diagnosed with non-obesity related Type 2 diabetes may have LADA. In some embodiments of the methods disclosed herein, the autoimmune disease comprises a decreased number of insulin-producing β-cells of the pancreas in a subject relative to a reference standard or normal control subject.

In some embodiments of the methods disclosed herein, the subject has been diagnosed with an autoimmune disease (e.g., autoimmune diabetes, e.g., Type 1 diabetes). In certain embodiments, the subject has been diagnosed with an autoimmune disease (e.g., autoimmune diabetes, e.g., Type 1 diabetes) for less than 3 months, less than 6 months, less than 9 months, less than 1 year, or less than 1.5 years.

Additionally or alternatively, in some embodiments of the methods disclosed herein, the subject has detectable levels of autoimmune antibody but has not developed symptoms of autoimmune disease (e.g., autoimmune diabetes, e.g., Type 1 diabetes), such as hyperglycemia. The autoimmune antibody may be specific for an islet-autoantigen. For example, in some embodiments, the islet-autoantigen comprises insulin. In other embodiments, the autoimmune antibody is an anti-insulin antibody.

In certain embodiments of the methods disclosed herein, the subject has no detectable levels of insulin autoantibody and has not developed symptoms of autoimmune disease (e.g., autoimmune diabetes, e.g., Type 1 diabetes), e.g., has not developed hyperglycemia.

In some embodiments of the methods disclosed herein, the subject has no detectable levels of a pathogenic B cell population or a disease-causing B cell population (e.g., anti-insulin B cells, insulin-specific B cells, or insulin$^+$B cells) and has not developed symptoms of autoimmune disease (e.g., autoimmune diabetes, e.g., Type 1 diabetes), e.g., has not developed hyperglycemia.

In certain embodiments of the methods disclosed herein, the subject has detectable levels of a pathogenic B cell population or a disease-causing B cell population (e.g., anti-insulin B cells, insulin-specific B cells, or insulin$^+$B cells) but has not developed symptoms of autoimmune disease (e.g., autoimmune diabetes, e.g., Type 1 diabetes), e.g., has not developed hyperglycemia. In some embodiments, the B cell population comprises an insulin-specific B cell. In some embodiments, the insulin-specific B cell presents a specific cell surface receptor such as B220, CD19, CD20, CD22, or other similar cell surface receptors and isoforms thereof. In certain embodiments, the insulin-specific B cell expresses two or more cell surface receptors such as B220, CD19, CD20, CD22, and other similar cell surface receptors and isoforms thereof.

Additionally or alternatively, in some embodiments of the methods disclosed herein, the level of endogenous C-peptide in a subject is assessed to aid in the diagnosis and extent of autoimmune diabetes (e.g., Type 1 diabetes or latent autoimmune diabetes). C-peptide is frequently utilized as a biomarker for residual β cell function, as it is produced in equal amounts to insulin and may therefore represent the total amount of insulin secretion in a subject (Jones, A. G. and Hattersley, A. T., *Diabet Med* (2013) 30, 803-817). Measurement of C-peptide in a subject may be useful in directing determination of insulin levels, as any exogenous insulin present in a subject will be also detected in direct insulin assays. A healthy subject (e.g., a subject without autoimmune diabetes) has an endogenous C-peptide level that ranges from about 0.6 nmol/L to about 0.8 nmol/L (e.g., about 0.65 nmol/L). In contrast, a subject with autoimmune diabetes (e.g., Type 1 diabetes or LADA) has an endogenous C-peptide level ranging from undetectable to about 0.6 nmol/L (e.g., about 0.05 nmol/L).

In some embodiments, the subject has been diagnosed with autoimmune diabetes (e.g., Type 1 diabetes) and has an endogenous C-peptide level of equal to or less than about 0.01 nmol/L, about 0.02 nmol/L, about 0.03 nmol/L, about 0.04 nmol/L, about 0.05 nmol/L, about 0.06 nmol/L, about 0.07 nmol/L, about 0.08 nmol/L, about 0.09 nmol/L, about 0.1 nmol/L, about 0.125 nmol/L, about 0.15 nmol/L, about 0.175 nmol/L, about 0.2 nmol/L, about 0.3 nmol/L, about 0.4 nmol/L, or about 0.5 nmol/L, or less than 0.6 nmol/L e.g., before treatment with a conjugate described herein.

In some embodiments, the subject has been diagnosed with autoimmune diabetes (e.g., Type 1 diabetes) and has an endogenous C-peptide level of less than or equal to about 0.1 nmol/L, about 0.09 nmol/L, about 0.08 nmol/L, about 0.07 nmol/L, about 0.06 nmol/L, about 0.05 nmol/L, about 0.04 nmol/L, about 0.03 nmol/L, about 0.02 nmol/L, about 0.01 nmol/L, or less, e.g., before treatment with a conjugate described herein. In some embodiments, the subject has been diagnosed with autoimmune diabetes (e.g., Type 1 diabetes) and has an endogenous C-peptide level of less than or equal to about 0.01 nmol/L, about 0.009 nmol/L, about 0.008 nmol/L, about 0.007 nmol/L, about 0.006 nmol/L, about 0.005 nmol/L, about 0.004 nmol/L, about 0.003 nmol/L, about 0.002 nmol/L, about 0.001 nmol/L, or less, e.g., before treatment with a conjugate described herein. In some embodiments, the subject has been diagnosed with autoimmune diabetes (e.g., Type 1 diabetes) and has an endogenous C-peptide level of less than or equal to about 0.001 nmol/L, about 0.1 pmol/L, about 0.01 pmol/L, about 0.001 pmol/L, or less, e.g., before treatment with a conjugate described herein. In certain embodiments, the subject has been diagnosed with autoimmune diabetes (e.g., Type 1 diabetes) and has an undetectable level of endogenous C-peptide, e.g., before treatment with a conjugate described herein.

In some embodiments, the subject has been diagnosed with autoimmune diabetes (e.g., Type 1 diabetes) and has an endogenous C-peptide level of about 95% or less relative to a reference standard, e.g., before treatment with a conjugate described herein. In some embodiments, the subject has been diagnosed with autoimmune diabetes (e.g., Type 1 diabetes) and has an endogenous C-peptide level of about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, or about 1% or less relative to a reference standard.

In some embodiments, the endogenous C-peptide level may be measured in a subject in a fasting (e.g., deprived of glucose) or fed (e.g., stimulated with glucose) state. By way of example, a subject in a fasting state may abstain from food for about 30 minutes, about 1 hour, about 2 hours, about 4 hours, about 6 hours, about 8 hours, about 12 hours, about 18 hours, about 20 hours, or about 24 hours prior to analysis of the endogenous C-peptide level. In another example, a subject in a fed state may consume food within 12 hours, within 10 hours, within 6 hours, within 4 hours, within 3 hours, within 2 hours, within 1.5 hours, within 1 hour, within 30 minutes, within 15 minutes, or concurrent with analysis of the endogenous C-peptide level.

In some embodiments, the subject is in a fasted (e.g., deprived of glucose) state and has an undetectable level of endogenous C-peptide, e.g., prior to treatment with a conjugate described herein. In some embodiments, the subject is in a fasted (e.g., deprived of glucose) state and has an endogenous C-peptide level less than or equal to about 0.06 nmol/L, e.g., prior to treatment with a conjugate described herein. In some embodiments, the subject is in a fasted (e.g., deprived of glucose) state and has an endogenous C-peptide level less than or equal to about 0.06 nmol/L, about 0.07 nmol/L, about 0.08 nmol/L, about 0.09 nmol/L, about 0.1 nmol/L, about 0.125 nmol/L, about 0.15 nmol/L, about 0.175 nmol/L, about 0.2 nmol/L, about 0.3 nmol/L, about 0.4 nmol/L, about 0.5 nmol/L, about 0.6 nmol/L, about 0.7 nmol/L, about 0.8 nmol/L, about 0.9 nmol/L, about 1.0 nmol/L or more, e.g., prior to treatment with a conjugate described herein. In some embodiments, the subject is in a fasted state and has an endogenous C-peptide level of less than or equal to about 0.2 nmol/L, or less than or equal to about 0.5 nmol/L, or less than or equal to about 1.0 nmol/L, e.g., prior to treatment with a conjugate described herein.

In some embodiments, the subject is in a fed (e.g., stimulated with glucose) state and has an undetectable level of endogenous C-peptide, e.g., prior to treatment with a conjugate described herein. In some embodiments, the subject is in a fed (e.g., stimulated with glucose) state and has an endogenous C-peptide level less than or equal to about 0.2 nmol/L, e.g., prior to treatment with a conjugate described herein. In other embodiments, the subject is in a fed state (e.g., stimulated with glucose) state and has an endogenous C-peptide level less than or equal to about 0.2 nmol/L, about 0.25 nmol/L, about 0.3 nmol/L, about 0.4 nmol/L, about 0.5 nmol/L, about 0.6 nmol/L, about 0.7 nmol/L, about 0.8 nmol/L, about 0.9 nmol/L, about 1.0 nmol/L, or more, e.g., prior to treatment with a conjugate described herein. In certain embodiments, the subject is in a fed state and has an endogenous C-peptide level of less than or equal to about 0.6 nmol/L, or less than or equal to about 0.75 nmol/L, or less than or equal to about 1.0 nmol/L, e.g., prior to treatment with a conjugate described herein.

In some embodiments, the conjugate is administered prophylactically. In some embodiments, the subject has no detectable levels of an autoimmune antibody (e.g., an insulin autoantibody) and the conjugate is administered prophylactically. In some embodiments, the subject has no detectable levels of a pathogenic B cell population or a disease-causing B cell population (e.g., anti-insulin B cells, insulin-specific B cells, or insulin$^+$B cells) and the conjugate is administered prophylactically. In some embodiments, the subject has no detectable levels of an autoimmune antibody (e.g., an insulin autoantibody) and no detectable levels of a pathogenic B cell population or a disease-causing B cell population (e.g., anti-insulin B cells, insulin-specific B cells, or insulin$^+$B cells) and the conjugate is administered prophylactically. In some embodiments, the subject has not been diagnosed with an autoimmune disease (e.g., autoimmune diabetes, e.g., Type 1 diabetes). In some embodiments, the subject has not been diagnosed with an autoimmune disease (e.g., autoimmune diabetes, e.g., Type 1 diabetes) and the conjugate is administered prophylactically. In some embodiments, the subject is at risk for developing T1D, e.g., the subject has a first degree relative who has been diagnosed with T1D. The subject may be an adult, or a child.

In some embodiments, the subject is at risk for developing T1D, e.g., the subject has one or more alleles at the DRB1, DQA1, and/or DQB1 loci (e.g., DR-DQ haplotypes) that are associated with higher risk for developing T1D, e.g., as described in Erlich, et al., *Diabetes.* 2008 April; 57(4): 1084-1092, incorporated herein by reference. In some embodiments, the subject has one or more of the following human leukocyte antigen (HLA) haplotypes:

(a) DRB1*0301-DQA1*0501-DQB1*0201
(b) DRB1*0405-DQA1*0301-DQB1*0302

(c) DRB1*0401-DQA1*0301-DQB*0302
(d) DRB1*0402-DQA1*0301-DQB1*0302
(e) DRB1*0404-DQA1*0301-DQB1*0302; or
(f) DRB1*0801-DQB1*0401-DQB1*0402.

In some embodiments, upon administration of the conjugate, the subject does not develop symptoms of an autoimmune disease (e.g., autoimmune diabetes, e.g., Type 1 diabetes). In some embodiments, upon administration of the conjugate, the subject does not develop symptoms of an autoimmune disease (e.g., autoimmune diabetes, e.g., Type 1 diabetes) for at least about 3 months, at least about 6 months, at least about 9 months, at least about 1 year, at least about 1.5 years, at least about 2 years, at least about 3 years, at least about 4 years, at least about 5 years, at least about 10 years, at least about 15 years, at least about 20 years, at least about 25 years, at least about 30 years, at least about 40 years, at least about 50 years or more.

In some embodiments, upon administration of the conjugate, the subject does not develop an autoimmune disease (e.g., autoimmune diabetes, e.g., Type 1 diabetes). In some embodiments, upon administration of the conjugate, the subject does not develop an autoimmune disease (e.g., autoimmune diabetes, e.g., Type 1 diabetes) for at least about 3 months, at least about 6 months, at least about 9 months, at least about 1 year, at least about 1.5 years, at least about 2 years, at least about 3 years, at least about 4 years, at least about 5 years, at least about 10 years, at least about 15 years, at least about 20 years, at least about 25 years, at least about 30 years, at least about 40 years, at least about 50 years or more.

In some embodiments, upon administration of the conjugate, the subject has a delayed rate of onset of the symptoms of autoimmune disease (e.g., autoimmune diabetes, e.g., Type 1 diabetes) compared with a reference standard or reference treatment. In some embodiments, upon administration of the conjugate, the rate of onset of autoimmune disease (e.g., autoimmune diabetes, e.g., Type 1 diabetes) is delayed by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared with a reference standard or reference treatment. In some embodiments, upon administration of the conjugate, the rate of onset of the symptoms of autoimmune disease (e.g., autoimmune diabetes, e.g., Type 1 diabetes) is delayed by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared with a reference standard or reference treatment.

In some embodiments, upon administration of the conjugate, the subject has a delayed rate of onset of autoimmune disease (e.g., autoimmune diabetes, e.g., Type 1 diabetes) compared with a reference standard or reference treatment. In some embodiments, upon administration of the conjugate, the rate of onset of autoimmune disease (e.g., autoimmune diabetes, e.g., Type 1 diabetes) is delayed by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared with a reference standard or reference treatment. In some embodiments, upon administration of the conjugate, the rate of onset of autoimmune disease (e.g., autoimmune diabetes, e.g., Type 1 diabetes) is delayed by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared with a reference standard or reference treatment.

In some embodiments, the conjugate is administered therapeutically. In some embodiments, the subject has detectable levels of an autoimmune antibody (e.g., an insulin autoantibody) and the conjugate is administered therapeutically. In some embodiments, the subject has detectable levels of a pathogenic B cell population or a disease-causing B cell population (e.g., anti-insulin B cells, insulin-specific B cells, or insulin$^+$B cells) and the conjugate is administered therapeutically. In some embodiments, the subject has detectable levels of an autoimmune antibody (e.g., an insulin autoantibody) and detectable levels of a pathogenic B cell population or a disease-causing B cell population (e.g., anti-insulin B cells, insulin-specific B cells, or insulin$^+$B cells) and the conjugate is administered therapeutically. In some embodiments, the subject has been diagnosed with an autoimmune disease (e.g., autoimmune diabetes, e.g., Type 1 diabetes). In some embodiments, the subject has been diagnosed with an autoimmune disease (e.g., autoimmune diabetes, e.g., Type 1 diabetes) and the conjugate is administered therapeutically.

In some embodiments, administration of the conjugate treats, reverses, or ameliorates the symptoms of autoimmune disease (e.g., autoimmune diabetes, e.g., Type 1 diabetes) in a subject compared to that observed in the subject prior to administration. In some embodiments, upon administration of the conjugate, the symptoms of autoimmune disease (e.g., autoimmune diabetes, e.g., Type 1 diabetes) in a subject are treated, reversed, or ameliorated by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared to that observed in the subject prior to administration. In certain embodiments, upon administration of the conjugate, the symptoms of autoimmune disease (e.g., autoimmune diabetes, e.g., Type 1 diabetes) in a subject are treated, reversed, or ameliorated by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared to that observed in the subject prior to administration.

In some embodiments, administration of the conjugate treats, reverses, or ameliorates an autoimmune disease (e.g., autoimmune diabetes, e.g., Type 1 diabetes) in a subject compared to that observed in the subject prior to administration. In some embodiments, upon administration of the conjugate, the autoimmune disease (e.g., autoimmune diabetes, e.g., Type 1 diabetes) in the subject is treated, reversed, or ameliorated by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared to that observed in the subject prior to administration. In certain embodiments, upon administration of the conjugate, the autoimmune disease (e.g., autoimmune diabetes, e.g., Type 1 diabetes) in the subject is treated, reversed, or ameliorated by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared to that observed in the subject prior to administration.

In some embodiments, the subject receives one course of treatment of a conjugate described herein. A course of treatment as used herein refers to a particular dosage amount or regimen as determined by a suitable practitioner provided to a subject until the autoimmune disease (e.g., autoimmune diabetes e.g., Type 1 diabetes) is treated, cured, alleviated, or the symptoms are reduced. In other embodiments, the subject receives more than one course of treatment of a conjugate. In other embodiments, the subject receives a plurality of courses of treatment of a conjugate. In still other embodiments, the subject receives a plurality of courses of treatment of a conjugate, and each course of treatment is separated by a specific length of time (e.g., about 1 day, about 1 week, about 2 weeks, about 1 month, about 2 months, about 3 months, about 6 months, about 1 year, about 1.5 years, about 2 years, about 3 years, about 4 years, about 5 years, about 7.5 years, about 10 years, about 12.5 years, about 15 years, about 20 years or more).

In some embodiments, the subject is an adult (e.g., at least 18 years of age, e.g., at least 19, 20, 21, 22, 23, 24, 25, 25-30, 30-35, 35-40, 40-50, 50-60, 60-70, 70-80, or 80-90 years of age). In some embodiments, the subject is a child (e.g., less than 18 years of age, e.g., less than 17, 16, 15, 14, 13, 12, 11, 10, 9, 8, 7, 6, 5, 4, 3, 2, 1 or less years of age). In some embodiments, the subject is a male or a female.

In some embodiments, a reference treatment used in any method described herein includes but is not limited to an insulin or insulin analog, e.g., an insulin or insulin analog described herein; islet cell transplantation; pancreas transplantation; or antibody (e.g., cytotoxic antibody) against a pan-B cell antigen (e.g., anti-CD20 antibody, anti-CD22 antibody, or anti-CD19 antibody). In some embodiments, a reference treatment can include a naturally occurring insulin (e.g., proinsulin or mature insulin) from a mammal, e.g., human or mouse or compositions described in US 2013/0028918 A1 or CN 103509118A.

In some embodiments, a reference standard used in any method described herein includes an outcome, e.g., outcome described herein, of an autoimmune disease therapy, e.g., type 1 diabetes therapy. In some embodiments, a reference standard is a level of a marker (e.g., blood glucose or level of C peptide) in the subject prior to initiation of a therapy, e.g., a conjugate therapy described herein, e.g., where the subject is at risk for developing T1D (e.g., subject is a first degree relative of a T1D patient); where the subject is pre-diabetic (e.g., subject is autoantibody positive); where the subject has experienced a recent onset of T1D (e.g., time from onset of less than 12 months); where the subject has long-standing T1D (e.g., time from onset greater than or equal to 12 months); or where the subject is a healthy subject (e.g., healthy age and/or sex-matched subject). In some embodiments, a reference standard is a measure of presence of/progression of/severity of disease or presence of/severity of symptoms of disease prior to initiation of a therapy, e.g., a conjugate therapy described herein, e.g., where the subject is at risk for developing T1D (e.g., subject is a first degree relative of a T1D patient); where the subject is pre-diabetic (e.g., subject is autoantibody positive); where the subject has experienced a recent onset of T1D (e.g., time from onset of less than 12 months); where the subject has long-standing T1D (e.g., time from onset greater than or equal to 12 months); or where the subject is a healthy subject (e.g., healthy age and/or sex-matched subject).

Pharmaceutical Compositions

Provided herein are pharmaceutical compositions containing a conjugate described herein that can be used to induce anergy in insulin-binding B cells and/or treat or prevent an autoimmune disease, e.g., autoimmune diabetes, e.g., Type 1 diabetes.

The amount and concentration of the conjugate in pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes, see Chapter 25.3 in Volume 5 of Comprehensive Medicinal Chemistry (Corwin Hansch; Chairman of Editorial Board), Pergamon Press 1990.

Provided herein are pharmaceutical compositions containing a conjugate described herein that can be used to induce anergy in insulin-binding B cells and/or treat or prevent an autoimmune disease, e.g., autoimmune diabetes, e.g., Type 1 diabetes.

While it is possible for a conjugate described herein to be administered alone, in some embodiments, the conjugate of the present technology may be administered as a pharmaceutical formulation (composition), where the conjugate is combined with one or more pharmaceutically acceptable diluents, excipients or carriers. The pharmaceutical compositions having one or more conjugates disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

The conjugate may be formulated for administration in any convenient way for use in human medicine. In certain embodiments, the conjugate included in the pharmaceutical preparation may be active itself, or may be a prodrug, e.g., capable of being converted to an active compound in a physiological setting. Regardless of the route of administration selected, the conjugate of the present technology, which may be used in a suitable hydrated form, and/or the pharmaceutical compositions of the present technology, is formulated into a pharmaceutically acceptable dosage form described herein or by other conventional methods known to those of skill in the art.

In another aspect, the present technology provides pharmaceutically acceptable compositions comprising a therapeutically effective amount or prophylactically effective amount of a conjugate described herein, formulated together with one or more pharmaceutically acceptable carriers (additives) and/or diluents. The pharmaceutical compositions described herein can be specially formulated for administration in solid or liquid form, including those adapted for parenteral administration, for example, by subcutaneous, intramuscular or intravenous injection as, for example, a sterile solution or suspension. In certain embodiments, the pharmaceutical compositions can be simply dissolved or suspended in sterile water. In some embodiments, the pharmaceutical preparation is non-pyrogenic, i.e., does not elevate the body temperature of a patient.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations. In some embodiments, the carrier includes phosphate buffered saline (PBS).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

As described herein, certain embodiments of the conjugates of the present technology can contain a basic functional group, such as an amine, and are thus capable of forming pharmaceutically acceptable salts with pharmaceutically acceptable acids. The term "pharmaceutically acceptable salts" in these instances, refers to the relatively non-toxic, inorganic and organic acid addition salts of the conjugates of the present technology. These salts can be prepared in situ during the final isolation and purification of the conjugate, or by separately reacting a purified conjugate described herein in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

In other cases, certain embodiments of the conjugates of the present technology can contain one or more acidic functional groups and, thus, are capable of forming pharmaceutically acceptable salts with pharmaceutically acceptable bases. These salts can likewise be prepared in situ during the final isolation and purification of the conjugate, or by separately reacting the purified conjugate in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, from about 5 percent to about 70 percent, or from about 10 percent to about 30 percent.

Pharmaceutical compositions of the present technology suitable for parenteral administration comprise conjugates described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the present technology include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, in order to prolong the effect of the conjugate, it may be desirable to slow the absorption of the drug from the subcutaneous or intramuscular injection site. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered form of the conjugate is accomplished by dissolving or suspending the conjugate in an oil vehicle. Alternatively, absorption of the drug may be delayed through the use of a concentrated form of the conjugate.

In some embodiments, the conjugate is administered as a bolus infusion or an intravenous push. In some embodiments, the conjugate is administered through syringe injection, pump, pen, needle, or indwelling catheter.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal/topical means. For transmucosal or transdermal/topical administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or inhalants. For transdermal/topical administration, the active compounds are formulated into powders, solutions, ointments, lotions, gels, patches, pastes, salves, or creams as generally known in the art. The active compound can be mixed under sterile conditions with a pharmaceutically acceptable carrier, and with any preservatives, buffers, or propellants that may be required. In one embodiment, transdermal administration may be performed by iontophoresis.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

The present technology contemplates formulation of the conjugate in any of the aforementioned pharmaceutical compositions and preparations. Furthermore, the present technology contemplates administration via any of the foregoing routes of administration. One of skill in the art can select the appropriate formulation and route of administration based on the condition being treated and the overall health, age, and size of the patient being treated.

Effective Dosages

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ as determined in cell culture. Such information can be used to determine useful doses in humans accurately. Levels in plasma may be measured, for example, by high performance liquid chromatography.

Actual dosage levels of the conjugate in the pharmaceutical compositions described herein can be varied so as to obtain an amount of the active ingredient that is effective to achieve the desired therapeutic or prophylactic response for a particular patient, composition, and mode of administration, without being toxic to the patient.

The selected dosage level will depend upon a variety of factors including the activity of the particular conjugate employed, or the ester, salt or amide thereof, the route of administration, the time of administration, the rate of excretion of the particular conjugate being employed, the duration of the treatment, other drugs, compounds and/or materials used in combination with the particular conjugate employed, the severity of the disease or disorder, previous treatments, the age, sex, weight, condition, general health and prior medical history of the patient being treated, and like factors well known in the medical arts. Moreover, treatment of a subject with a therapeutically or prophylactically effective amount of the pharmaceutical compositions described herein can include a single treatment or a series of treatments.

A physician having ordinary skill in the art can readily determine and prescribe the effective amount of the pharmaceutical composition required. For example, the physician could start doses of the conjugate employed in the pharmaceutical composition at levels lower than that required in order to achieve the desired therapeutic or prophylactic effect and gradually increase the dosage until the desired effect is achieved. When the conjugate is administered as a pharmaceutical, to a subject, it can be given per se or as a pharmaceutical composition containing, for example, 0.1 to 99.5% (or 0.5 to 90%) of active ingredient in combination with a pharmaceutically acceptable carrier.

In general, a suitable daily dose of a conjugate will be that amount of the conjugate that is the lowest dose effective to produce a therapeutic effect. Such an effective dose will generally depend upon the factors described above. Typically, an effective amount of the one or more conjugates disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more conjugate concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime. In some embodiments, a therapeutically effective amount of one or more conjugates may be defined as a concentration of conjugate at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

Generally, intravenous and subcutaneous doses of the conjugate for a patient will range from about 0.0001 to about 100 mg per kilogram of body weight per day, e.g., about 0.0001-about 0.001 mg/kg/day, about 0.001-about 0.01 mg/kg/day, about 0.01-about 0.1 mg/kg/day, about 0.1-about 1 mg/kg/day, about 1-about 10 mg/kg/day, or about 10-about 100 mg/kg/day. In some embodiments, the conjugate is administered at a dose greater than or equal to 60 nmol/kg/day. In some embodiments, the conjugate is administered at a dose greater than or equal to 75 nmol/kg/day, greater than or equal to 100 nmol/kg/day, greater than or equal to 150 nmol/kg/day, or greater than or equal to 200 nmol/kg/day. In certain embodiments, the conjugate is administered at a dose greater than or equal to 1 mg/kg/day, e.g., 2 mg/kg/day, 4 mg/kg/day, 8 mg/kg/day, 16 mg/kg/day, 32 mg/kg/day, 64 mg/kg/day, 100 mg/kg/day, 200 mg/kg/day or greater.

The conjugate may be present at a concentration of about 100 mg/mL or less (e.g., 100 mg/mL or less, e.g., 90 mg/mL, 80 mg/mL, 70 mg/mL, 60 mg/mL, 50 mg/mL, 40 mg/mL, 30 mg/mL, 20 mg/mL, 10 mg/mL, 5 mg/mL, 2.5 mg/mL, 1 mg/mL, 0.5 mg/mL, 0.25 mg/mL, 0.1 mg/mL, 0.05 mg/mL, 0.01 mg/mL, or less). In some embodiments, the conjugate is present at a concentration of about 0.25 mg/mL to about 1 mg/mL, e.g., about 0.25 mg/mL, about 0.5 mg/mL (e.g., 0.5 mg/mL), about 0.75 mg/mL, or about 1 mg/mL.

If desired, the effective daily dose of the conjugate can be administered as two, three, four, five, six or more sub-doses administered separately at appropriate intervals throughout the day, optionally, in unit dosage forms. In some embodiments, the conjugate is administered once daily. In some embodiments, the conjugate is administered at least twice a week. In some embodiments, the conjugate is administered at least once a week. In certain embodiments, the conjugate is administered twice weekly.

The conjugate can be administered as such or in admixtures with pharmaceutically acceptable and/or sterile carriers and can also be administered in conjunction with antimicrobial agents such as penicillins, cephalosporins, aminoglycosides and glycopeptides. Conjunctive therapy thus includes sequential, simultaneous and separate administration of the conjugate in a way that the therapeutic or prophylactic effects of the first administered therapy are still detectable when the subsequent therapy is administered.

Combination Therapy

In some embodiments, one or more conjugates disclosed herein may be combined with one or more additional therapies for inducing anergy in insulin-binding B cells and/or for the prevention or treatment of an autoimmune disease (e.g., autoimmune diabetes, e.g., Type 1 diabetes).

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to no more than four weeks. In addition, the combination methods, compositions and formulations are not to be limited to the use of only two agents.

In some embodiments, the at least one additional therapy is administered in a formulation comprising a combination with a conjugate described herein to treat or prevent an autoimmune disease (e.g., autoimmune diabetes, e.g., Type 1 diabetes). In certain embodiments, the at least one additional therapy is administered simultaneously with the conjugate described herein. In certain embodiments, the at least one additional therapy is administered sequentially (at a different time) than the conjugate described herein. In an example, the at least one additional therapy is administered about 5 minutes, about 10 minutes, about 30 minutes, about 1 hour, about 1.5 hours, about 2 hours, about 4 hours, about 6 hours, about 12 hours, about 18 hours, about 24 hours, about 2 days, about 3 days, about 4 days, about 5 days, about 6 days, about 1 week, about 2 weeks, about 3 weeks, about 4 weeks apart from the conjugate described herein. The at least one additional therapy may or may not be administered by the same route as the conjugate. In an example, the conjugate may be administered in one manner (e.g., intravenously or subcutaneously), while the at least one additional therapy may be separately administered in another manner (e.g., orally).

In some embodiments, the at least one additional therapy is an insulin sensitizer. Insulin sensitizers (e.g., biguanides (e.g., metformin) and glitazones (e.g., rosiglitazone and pioglitazone)) act by increasing the response of a subject to a given amount of insulin (or insulin analog). A patient receiving an insulin sensitizer may therefore require a lower dose of a conjugate described herein compared with a patient not receiving said insulin sensitizer. Thus, in certain embodiments, the conjugate is administered to a subject in combination with an insulin sensitizer. In some embodiments, the conjugate may be administered at about 95% of the standard dose required in the absence of the insulin sensitizer, e.g., at about 90%, at about 85%, about 80%, at about 75%, at about 70%, at about 65%, at about 60%, at about 55%, at about 50%, at about 50%, at about 45%, at about 40%, at about 35%, at about 30%, at about 25%, at about 20%, at about 15%, at about 10%, at about 5% or less of the standard dose required in the absence of the insulin sensitizer.

In some embodiments, the at least one additional therapy is administered to prevent full onset of an autoimmune disease (e.g., autoimmune diabetes, e.g., Type 1 diabetes) or the symptoms thereof and results in maintenance of at least about 90% β-cell mass compared with that of a healthy subject. In some embodiments, the at least one additional therapy is administered to prevent full onset of an autoimmune disease (e.g., autoimmune diabetes, e.g., Type 1 diabetes) and results in maintenance of at least about 80%, at least about 70%, at least about 60%, at least about 50%, at least about 40%, at least about 30%, at least about 20%, at least about 10%, or at least about 5% j-cell mass compared with that of a healthy subject. In some embodiments, the conjugate is administered to a subject in combination with a therapy that prevents the symptoms of an autoimmune disease (e.g., autoimmune diabetes, e.g., Type 1 diabetes) and results in maintenance of at least about 90% j-cell mass compared with that of a healthy subject. In some embodiments, the conjugate is administered to a subject in combination with a therapy that prevents the symptoms of an autoimmune disease (e.g., autoimmune diabetes, e.g., Type 1 diabetes) and results in maintenance of at least about 80%, at least about 70%, at least about 60%, at least about 50%, at least about 40%, at least about 30%, at least about 20%, at least about 10%, or at least about 5% j-cell mass compared with that of a healthy subject.

In some embodiments, the at least one additional therapy is administered to prevent full onset of an autoimmune disease (e.g., autoimmune diabetes, e.g., Type 1 diabetes) or the symptoms thereof and results in maintenance of at least about 90% endogenous C-peptide level compared with that of a healthy subject. In some embodiments, the at least one additional therapy is administered to prevent full onset of an autoimmune disease (e.g., autoimmune diabetes, e.g., Type 1 diabetes) or the symptoms thereof and results in maintenance of at least about 80%, at least about 70%, at least about 60%, at least about 50%, at least about 40%, at least about 30%, at least about 20%, at least about 10%, or at least about 5% endogenous C-peptide level compared with that of a healthy subject. In some embodiments, the conjugate is administered to a subject in combination with a therapy that prevents the symptoms of an autoimmune disease (e.g., autoimmune diabetes, e.g., Type 1 diabetes) and results in maintenance of at least about 90% endogenous C-peptide level compared with that of a healthy subject. In some embodiments, the conjugate is administered to a subject in combination with a therapy that prevents the symptoms of an autoimmune disease (e.g., autoimmune diabetes, e.g., Type 1 diabetes) and results in maintenance of at least at least about 80%, at least about 70%, at least about 60%, at least about 50%, at least about 40%, at least about 30%, at least about 20%, at least about 10%, or at least about 5% endogenous C-peptide level compared with that of a healthy subject.

Kits

The present disclosure also provides kits for inducing anergy in insulin-binding B cells and/or for the prevention and/or treatment of an autoimmune disease (e.g., autoimmune diabetes, e.g., Type 1 diabetes) comprising one or more of the conjugates described herein, and optionally instructions for use. Optionally, the above described components of the kits of the present technology are packed in suitable containers and labeled for the prevention and/or treatment of an autoimmune disease (e.g., autoimmune diabetes, e.g., Type 1 diabetes).

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic or products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way.

Example 1: Materials and Methods

Protein and Plasmid Design. Vector selection (Pet9a), plasmid construct, and modified signal peptide sequence (MGSSHHHHHHHSSFLDPVLM (SEQ ID NO: 5)) are disclosed in R. B. Mackin (Mackin, R. B. *MethodsX* 2014, 1, 108-117), which describes the methods to express and purify correctly folded native proinsulin with yields above 15 mg/L culture (99% purity). Proinsulin expression in *E. coli* has several challenges including formation of insoluble inclusion bodies and preventing N-terminal degradation. Other articles address these challenges but do not exceed yields of 5 mg/L culture (Cowley, D. J.; Mackin, R. B. *FEBS Letters* 1997, 402, 124-130; Redwan, E. M. et al., *Preparative Biochemistry and Biotechnology* 2007, 38, 24-39), require fusion of proinsulin to other large proteins (Trabucchi, A et al., *Appl Microbiol Biotechnol* 2012, 94, 1565-1576; Winter, J. et al. *Journal of Biotechnology* 2000, 84, 175-185), or do not provide sufficient detail due to commercial interests (Tikhonov et al. *Protein Expression and Purification* 2001, 21, 176-182). A GGG-sortase N-terminal tag is fused directly to the proinsulin sequence without a peptide linker.

Proinsulin Expression and Purification: Human proinsulin and variants, herein referred to as proinsulins, were expressed in BL21(DE3) *E. coli* as a fusion protein with a precursor peptide, isolated as inclusion bodies by centrifugation, and the fusion peptide was cleaved by cyanogen bromide. Details of the proinsulin expression protocol are detailed below:

Day 1: Prepare media as following in baffled shake flasks: 10 g tryptone, 5 g yeast extract, 10 g NaCl per liter of ultrapure water. Low salt LB-Lennox pre-mixed media is mixed 20 g/liter plus 5 g NaCl per liter. LB-Luria broth pre-mixed media is mixed 25 g/liter without exceeding 50% flask volume with media. Prepare starter cultures as well as growth cultures (2×50 ml starter culture is sufficient for up to 4 L growth culture). Cover shake flasks with aluminum foil and autoclave on setting 2 (liquids, media, etc.) for ~80 minutes. Once cool, add 1000× Kanamycin antibiotic stock to starter cultures only and briefly swirl to mix. Add 1 µl 1000× stock per 1 ml of media. Inoculate starter cultures with frozen stock located in −80 deg. C. freezer. Use 200 ml pipet tip to scrape small ice crystal from vial and pipette mix in media. Place shake flasks in shaker incubator. Run at 30 deg. C. and 200 RPM overnight.

Day 2: Check growth of starter cultures. Add 1000× Kanamycin antibiotic stock to growth culture flasks and briefly swirl to mix. Add 1 µl 1000× stock per 1 ml of media. Inoculate growth cultures by adding 1% of growth culture volume of starter culture using stripette. 1% inoculation volume results in OD600 nm >0.6 in 2.0 hours. Return to shaker incubator. Run at 37 deg. C. and 200 RPM. For 1 L baffled flasks, se 160 RPM. At 1.5 hours, check OD600 nm (growth density) by removing 1 ml media from a flask and checking on UV-Vis spectrophotometer. Water is used as a blank. Induce by adding 1M IPTG stock to a final concentration of 0.5 mM when OD600 nm is between 0.6-0.9 and express for 3-4 hours.

Harvesting Proinsulin: Harvest *E. coli* by transferring media to 750 ml centrifuge bottles (blue screw top lids). Spin down in swinging bucket centrifuge at 4500 g for 45 minutes at 4 deg. C. Pour off supernatant being careful to not disturb the pelleted cells. Suspend cells from each centrifuge bottle in 20 ml lysis buffer (50 mM tris, 50 mM NaCl. pH 8, 0.5 mM EDTA, 5% glycerol, 1% Triton X100) without Triton X100. Transfer to 200 ml glass homogenization jar.

Inclusion Body Isolation: Homogenize on ice at 85% intensity for 2 minutes using 10 seconds on, 20 off method. Transfer contents evenly between four 50 ml falcon tubes. Centrifuge 8000 g 20 deg. C. for 15 minutes. Pour off supernatant. Suspend each falcon tube's contents with 40 ml lysis buffer with Triton X100. Repeat centrifugation and wash steps 2× more times (3× total). Suspend each pellet in 2 ml DI H$_2$O. Pipette mix and sonicate to resuspend. Freeze in −80 degrees to aid with dispersion.

Cleaving Signal Peptide from Proinsulin: Thaw and sonicate to suspend the pellet. Transfer to 250 ml round bottom flask with stir bar. Add 32 ml 88% formic acid (for 4 L batch). Processing 4 L of culture will yield 4 pellets, each in 50 ml falcon tube. In a fume hood, weigh out 1.6 g cyanogen bromide and transfer to flask. Close flask with rubber stopper, cover with aluminum foil, and stir at 200 rpm overnight at room temperature (RT).

Load rotational evaporator (Roto-Vap) cooling chamber with 3 lbs dry ice and approximately 200 ml acetone. Attach 50 ml round bottom flask containing CNBr cleavage product. Turn on vacuum pump and shut inlet port. Spin at 200 rpm and lower into RT water bath. Watch for "bumping" and counter by letting air in the inlet port. Once bumping has ceased, turn on water bath heat to 40 deg. C. Run until dry.

Reduction of Disulfide Bonds: Add 40 ml 6M guanidinum 500 mM Tris pH 8.1 to flask containing dried CNBr cleavage product and stir/sonicate until dissolved. Add stopper and parafilm to seal. Inject 0.6 ml beta-mercaptoethanol, then stir at RT for 10 minutes.

Purification of Reduced Proinsulin: Set up Prep-LC according to standard protocol using solvents with 0.05% TFA. Equilibrate column at 30% ACN. Acidify sample to pH 3-4 by adding 0.5 ml conc. HCl (12M). Monitor addition by pH meter/strip to avoid going below pH 2. Syringe filter 40 ml of reduced proinsulin solution through Millex AA 0.8 um MCE membrane filter (blue) or Millex GP 0.22 um PES membrane filter (green). Keep filtered solution on ice. Inject 4.5 ml volumes and collect major peak which elutes from 9-11.5 minutes (35 ml). Combine fractions and rotovap in 500 ml flask to remove ACN.

Refolding of Reduced Proinsulin: Add appropriate volume of 20× refold buffer to flask along with stir bar. Add 2 mM beta-mercaptoethanol and 2 mM L-cystine to flask. Add stopper and seal with parafilm. 1.5 µl BME, 5 mg L-cystine per 10 ml volume. Stir overnight at 4 deg. C. in the cold room.

Purification of Folded Proinsulin: Remove 0.2 ml using needle and syringe to check folding on analytical HPLC. Set up Prep-LC according to standard protocol using solvents with 0.05% TFA. Equilibrate column at 25% ACN. Add 5% ACN by volume and acidify to pH 3-4 using concentrated HCl. Monitor by pH meter. Syringe filter through Millex 0.22 µm filter. Keep filtered solution on ice. Stop pumps, and attach sample inlet line (pre-filled with sample) to Pump A (top). Load 50-80 ml of sample at 10 ml/min. Stop pumps, attach Solvent A inlet line (filled with water), and flush with 5% B for 8 minutes at 14 ml/min. Collect refolded proinsulin, which elutes at 9.5-12 minutes (35 ml), and improperly folded proinsulin, which elutes at 12-14.5 minutes (35 ml). Combine like fractions and rotovap in 500 ml flask to remove ACN. Transfer aqueous folded proinsulin to 50 ml falcon tubes. Freeze at −80 deg. C. then place on lyophilizer.

Analysis of Purified Folded Proinsulin: Weigh dried proinsulin on scale. Dissolve portion of sample in 0.02% formic acid at 1 mg/ml. Check absorbance using nanodrop to calculate protein concentration. Run on analytical HPLC and SDS-PAGE (native and reduced) to check purity. Analyze sample to mass spectrometry to confirm identity.

The proinsulins were denatured in 6 M guanidine and reduced by beta-mercaptoethanol (BME). Reduced proinsulins were purified by RP LC and refolded at 0.5 mg/ml in an oxidative buffer. Refolded proinsulins were purified by RP LC and lyophilized.

Sortase Ligation: Enhanced pentamutant sortase A (eSrtA) was expressed in *E. coli* and purified by Ni-IMAC. Ligations were typically performed with 100 µM Fc-LPETGGH$_6$ (SEQ ID NO: 12), proinsulin-LPETGGHG (SEQ ID NO: 6), or azide-linker-LPETGGHG (SEQ ID NO: 6); 100 µM GGG-proinsulin or GGG-linker-azide; and 10 µM enhanced sortase A (pentamutant) in tris-buffered saline, 20% DMSO, 6 mM CaCl$_2$), and 200 µM NiSO4 at 37° C. for 4 hours or RT for 16 hours. Reaction progress was monitored by HPLC with RP C4 and SEC columns. Ligated product was purified by RPLC or protein A.

Copper-catalyzed azide-alkyne cycloaddition (CuAAC): The proinsulin-PEG$_n$-alkyne conjugate was synthesized with 1 equivalent (eq.) proinsulin-azide, 4 eq. alkyne-PEG$_n$-alkyne, 1 eq. CuSO$_4$, 5 eq. THPTA, and 20 eq. sodium ascorbate. Proinsulin-PEG$_n$-alkyne was purified by RPLC. The final CuAAC reaction yielding the Fc/CD22L-conjugate was performed with 40 µM Fc-LPETGGG-azide (SEQ ID NO: 13) or 100 µM CD22L-azide, 4 eq. alkyne-PEG$_n$-proinsulin, 12 eq. CuSO$_4$, 60 eq. THPTA, and 240 eq. sodium ascorbate. Fc-PEG$_n$-proinsulin was purified by SEC. CD22L-PEG$_n$-proinsulin was purified by RPLC.

Example 2: Synthesis of Conjugates

Proinsulin-LPETGGG-PEG$_3$-N$_3$ ("LPETGGG" disclosed as SEQ ID NO: 13). A solution of 0.2 mM proinsulin-LPETGGHG (SEQ ID NO: 6), 0.8 mM GGG-PEG3-azide, 0.02 mM pentamutant sortase A, 10 mM CaCl$_2$), and 0.4 mM NiSO4 in a 50 mM Tris, 150 mM NaCl pH 8 buffer is stirred at room temperature for 2 hours. The reaction is quenched and acidified with 0.5% v/v 88% formic acid before the desired product is isolated by preparatory reverse phase liquid chromatography (Prep-LC) using a C18 stationary phase column. Rotational evaporation under reduced pressure is used to remove the acetonitrile before freezing and lyophilization to yield a white powder. An isolated yield of 80% with purity >95% is routinely achieved at 10+ mg scale. The product identity is confirmed by MALDI mass spectrometry.

Insulin-CD22L. A solution of 0.4 mM insulin-B29-alkyne, 0.48 mM mCD22L-N$_3$ or 0.48 mM hCD22L-N$_3$ (the structure for each provided below this paragraph), 0.4 mM CuSO$_4$, 2 mM tris-hydroxypropyltriazolylmethylamine (THPTA), and 8 mM sodium ascorbate in a 50 mM sodium phosphate buffer pH 7.6 with 20% DMSO by volume were stirred at room temperature for 2 hours. The reaction is quenched and acidified with an equal volume of 50 mM HCl before the desired product is isolated by Prep-LC using a C18 stationary phase column. Rotational evaporation under reduced pressure is used to remove the acetonitrile before freezing and lyophilization to yield a white powder. An isolated yield of 70% with purity >95% is routinely achieved at 5+ mg scale. The product identity was confirmed by MALDI mass spectrometry.

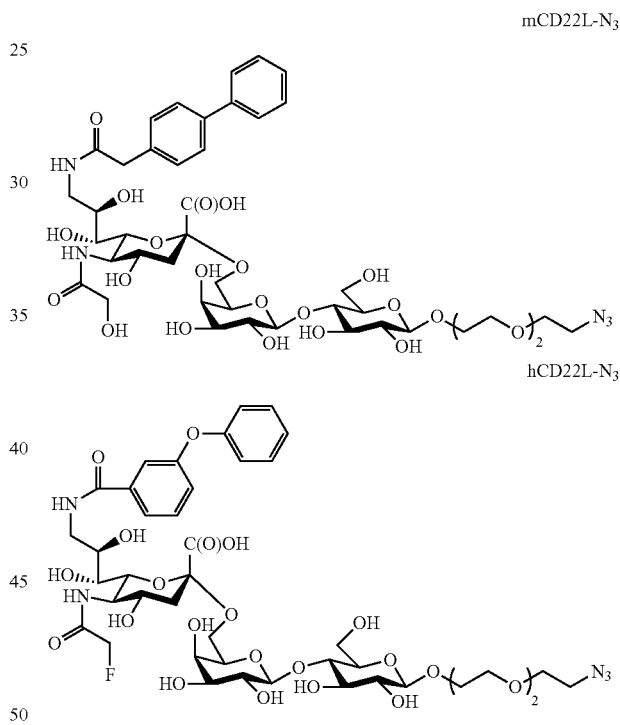

Conjugation of Insulin-B29-azide or Proinsulin-LPETG-N$_3$ (SEQ ID NO: 11) to PEG-alkyne. Synthesis was performed substantially in accordance with the procedures recited and cited to in Johnson, S. N. et al., *ACS Appl. Bio Mater.* 2020, 3, 6319-6330. A solution of 0.4 Mm PEG-alkyne (4-arm or bifunctional), 0.5 equivalents of insulin-B29-azide per alkyne or 0.5 equivalents of proinsulin-LPETG-N$_3$ (SEQ ID NO: 11) per alkyne, 0.8 mM CuSO$_4$, 4.0 mM THPTA, and 16 mM sodium ascorbate in a 50 mM sodium phosphate buffer pH 7.6 with 20% DMSO by volume were stirred at room temperature for 1 hour. The reaction is quenched and acidified with an equal volume of 50 mM HCl before the desired product is isolated by Prep-LC using a C18 stationary phase column. Discrete PEG-insulin conjugates are isolated from the mixture by collecting each peak separately. The 4-arm PEG(20K)- alkyne reactions yield, e.g., 4-arm PEG-insulin(1), 4-arm PEG-insulin(2), 4-arm PEG-insulin(3), and 4-arm PEG-insulin(4). The bifunctional PEG(10K)-alkyne reactions yield, e.g., bifunctional PEG-insulin(1) and bifunctional PEG-insulin(2). Rotational evaporation under reduced pressure is used to remove the acetonitrile before freezing and lyophilization to yield a white powder. The isolated products are >95% pure and their identity is confirmed by MALDI mass spectrometry. Data for exemplary synthesized products is presented in Table 1 below.

Conjugation of CD22L-$N_3$ to PEG-alkyne and PEG-insulin. Synthesis was performed substantially in accordance with the procedures recited and cited to in Johnson, S. N. et al., *ACS Appl. Bio Mater.* 2020, 3, 6319-6330. In particular, a solution of 0.1 mM PEG-alkyne or PEG-insulin (4-arm or bifunctional), 3 equivalents of m/hCD22L-$N_3$ per alkyne, 0.2 mM $CuSO_4$, 1.0 mM THPTA, and 4 mM sodium ascorbate in a 50 mM sodium phosphate buffer pH 7.6 with 2000 DMSO by volume were stirred at 37° C. for 2 hours. The reaction is quenched and acidified with an equal volume of 50 mM HCl before the desired product is isolated by Prep-LC using a C18 stationary phase column. Rotational evaporation under reduced pressure is used to remove the acetonitrile before freezing and lyophilization to yield a white powder. An isolated yield of 600% with purity >9500 is routinely achieved at a 5 mg scale. The product identity is confirmed by MALDI mass spectrometry. Data for exemplary synthesized products is presented in Table 1 below.

| Compound | MALDI (Da) |
|---|---|
| Bifunctional PEG(10K)-alkyne | 12011.6 |
| 4-arm PEG(20K)-alkyne | 20174.8 |
| Insulin-Alkyne | 5918.2 |
| Proinsulin-LPETGGHG (SEQ ID NO: 6) | 10138.5 |
| Proinsulin(F25D)-LPETGGHG (SEQ ID NO: 6) | 10105.6 |
| Proinsulin(F25D, Lispro)-LPETGGHG (SEQ ID NO: 6) | 10105.9 |
| Proinsulin(F25D, DKP)-LPETGGHG (SEQ ID NO: 6) | 10083.5 |
| Proinsulin(F25D, Lispro)-LPETGGG-PEG3-N3 (SEQ ID NO: 13) | 10169.8 |
| Proinsulin(F25D, DKP)-LPETGGG-PEG3-N3 (SEQ ID NO: 13) | 10147.2 |
| Bifunctional PEG(10K)-insulin(1) | 18288.5 |
| 4-arm PEG(20K)-insulin(1) | 26081.2 |
| 4-arm PEG(20K)-insulin(2) | 32332.7 |
| 4-arm PEG(20K)-insulin(3) | 38096.4 |
| Insulin-(alkyne/azide)-mCD22L | 6918.1 |
| Bifunctional PEG(10K)-mCD22L(2) | 13501.4 |
| Bifunctional PEG(10K)-Insulin(1)/mCD22L(1) | 18979.3 |
| Bifunctional PEG(10K)-insulin(2) | 24315.3 |
| 4-arm PEG(20K)-mCD22L(4) | 23608.5 |
| 4-arm PEG(20K)-insulin(1)/mCD22L(3) | 28823.15 |
| 4-arm PEG(20K)-insulin(2)/mCD22L(2) | 34140.8 |
| 4-arm PEG(20K)-insulin(3)/mCD22L(1) | 39395.9 |
| 4-arm PEG(20K)-insulin(4) | 44130.5 |
| 4-arm PEG(20K)-hCD22L(4) | 23506.9 |
| 4-arm PEG(20K)-insulin(1)/hCD22L(3) | 28981.3 |
| 4-arm PEG(20K)-insulin(2)/hCD22L(2) | 34295.8 |
| 4-arm PEG(20K)-insulin(3)/hCD22L(1) | 39122.7 |
| 4-arm PEG(20K)-Proinsulin | 61353.2 |
| 4-arm PEG(20K)-Proinsulin(F25D) | 61199.7 |
| 4-arm PEG(20K)-Proinsulin(F25D, Lispro) | 61082.2 |
| 4-arm PEG(20K)-Proinsulin(F25D, DKP) | 60807.7 |

Figures 2A, 2B:
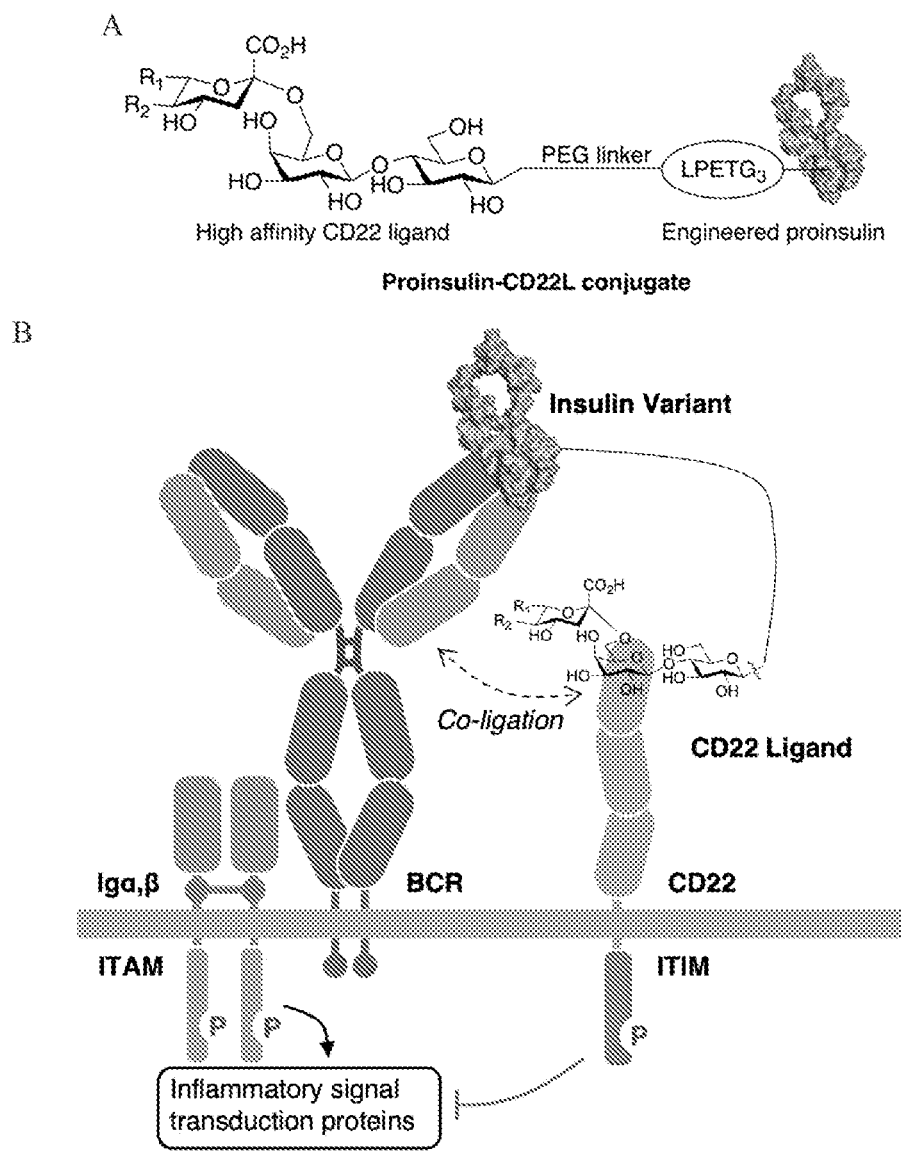
FIG. 2A: General design of the proinsulin-CD22L conjugates.
FIG. 2B: Co-ligation of the B cell receptor (BCR) to the immune inhibitory receptor CD22 to block B cell activation.
Figures 4A, 4B, 4C:
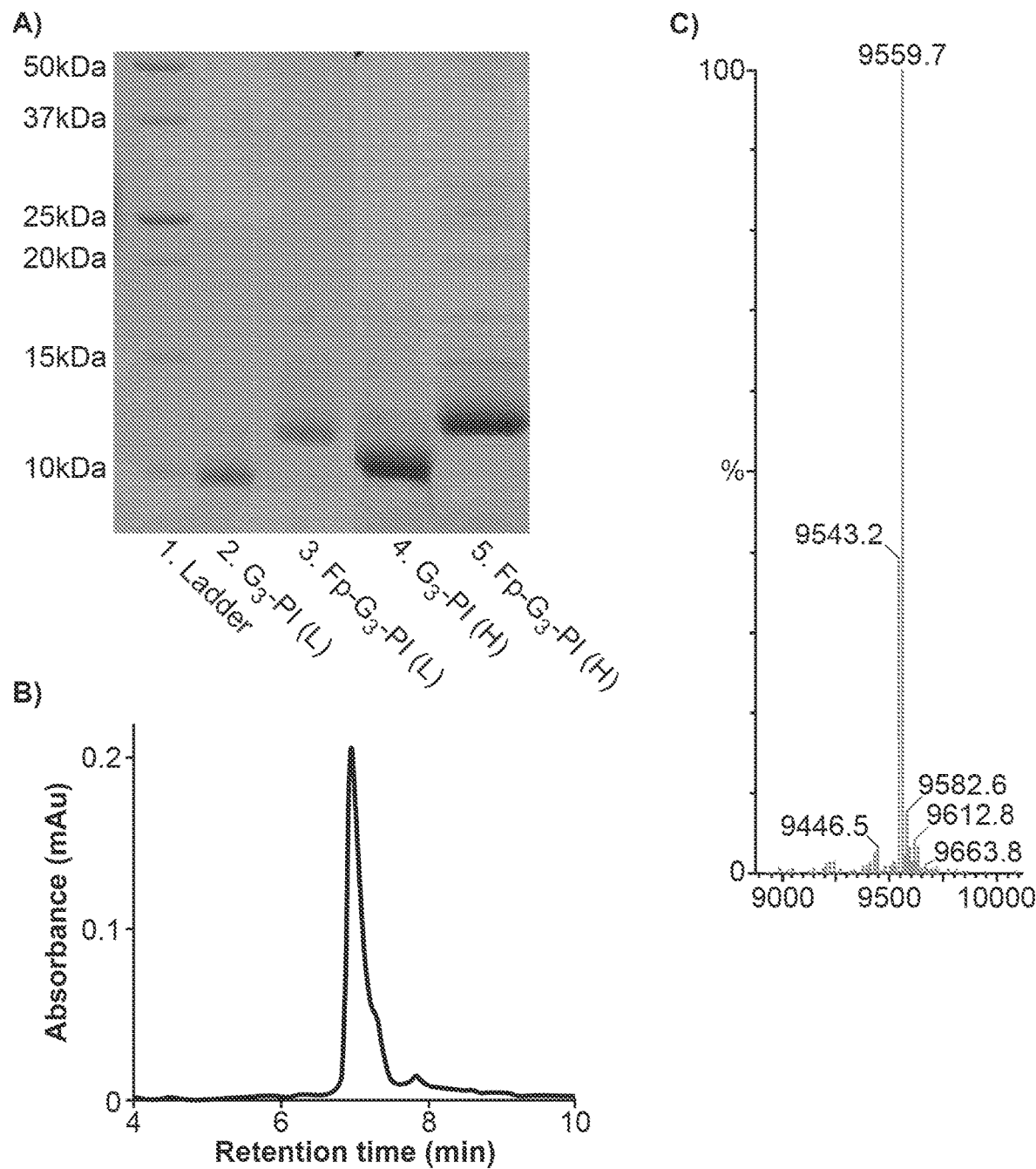
FIGS. 4A-4C: Analysis of $G_3$-proinsulin. Similar SDS-PAGE and HPLC analysis results acquired for all proinsulin variants but omitted for brevity.

Conjugates with the general form of Fc-$(proinsulin)_2$ and CD22L-proinsulin (FIG. 2) were designed. Five human proinsulins (FIG. 3) were expressed with titers of 40 mg/L of culture and purified to >9000 purity (FIG. 4) with a final yield of 5-10 mg/L: native proinsulin, $G_3$-proinsulin, $G_3$-proinsulin F25D, proinsulin-LPETG (SEQ ID NO: 11), and proinsulin-LPETG (SEQ TD NO: 11) F25D. The F25D mutation was incorporated to reduce binding to the insulin-receptor B to prevent hypoglycemia in future in vivo testing and was selected to minimally disrupt the T-cell and B-cell epitopes. Alkyne-PEG-alkynes with molecular weights of 10 and 20 kDa were purchased along with $G_3$-$PEG_3$-azide linker. An $N_3$-$PEG_3$-LPETGGHG (SEQ ID NO: 6) linker was synthesized from $N_3$-$PEG_3$-COOH and LPETGGHG (SEQ ID NO: 6) peptide. The $G_3$-proinsulin variants were ligated to an $N_3$-LPETGGHG (SEQ ID NO: 6) linker by eSrtA to give $N_3$-$G_3$-proinsulin (FIG. 5A) and an alkyne-LPETGGHG (SEQ TD NO: 6) linker to give alkyne-$G_3$-proinsulin (FIG. 5B).

Figure 6A:
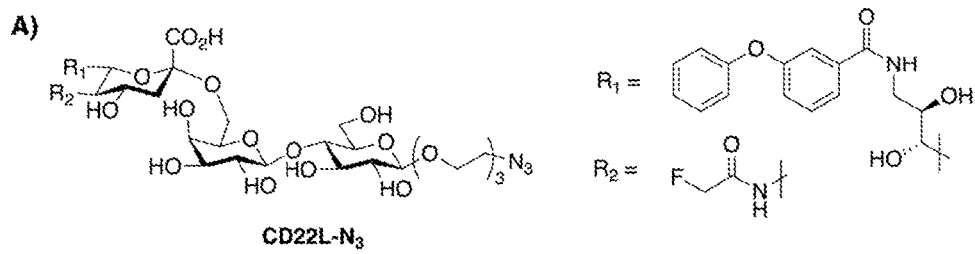
FIGS. 6A-6C: Proposed synthesis of CD22L-proinsulin conjugates.

A disubstituted sialic acid CD22 ligand, CD22L-$N_3$, (FIG. 6A) with an azide handle was synthesized.

Figures 5A, 5B, 5C:
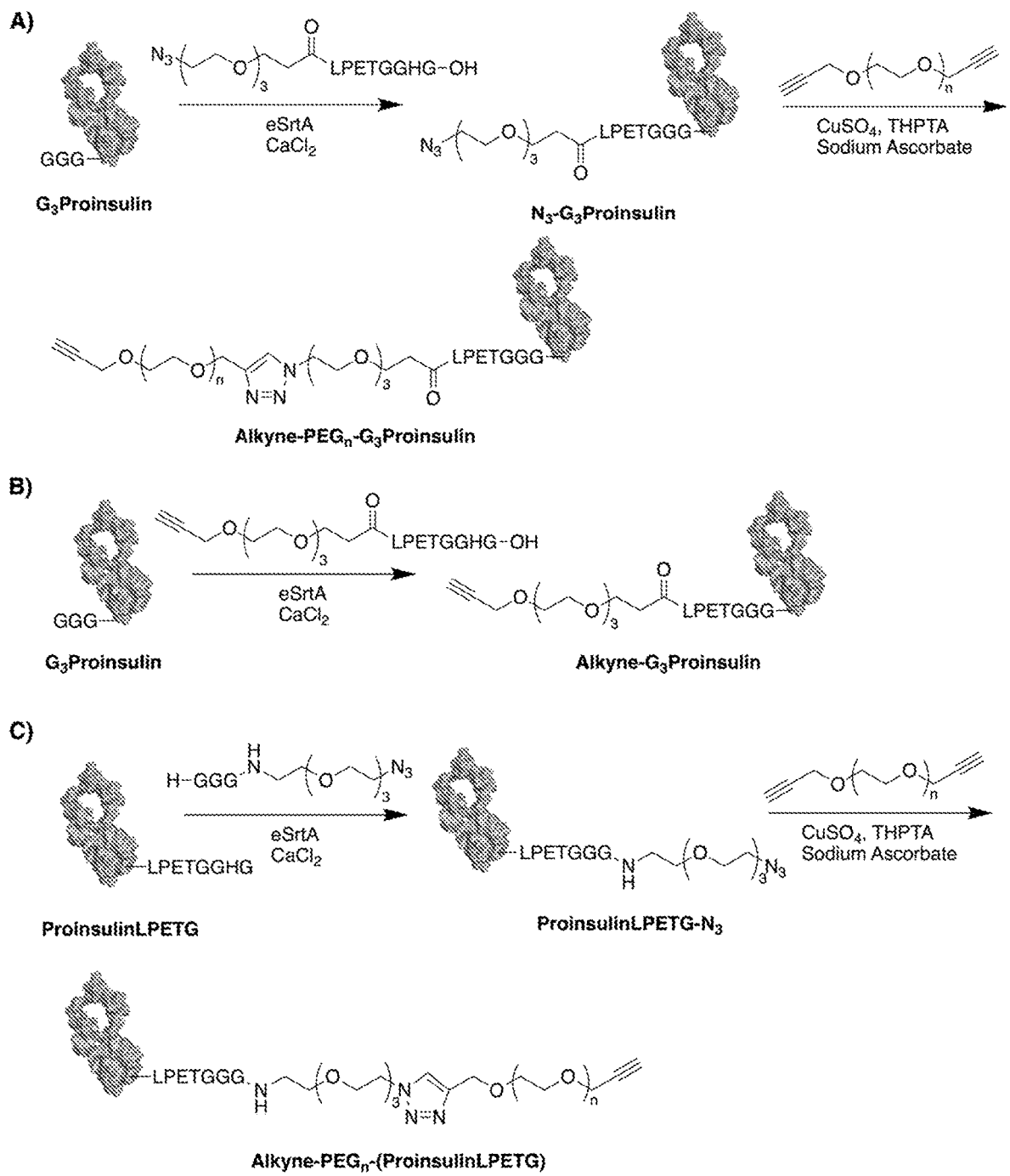
FIGS. 5A-5C: PEGylation of proinsulins via eSrtA ligation and CuAAC to give alkyne-functionalized species for CuAAC conjugation to azide-functionalized CD22L.
Figure 6B:
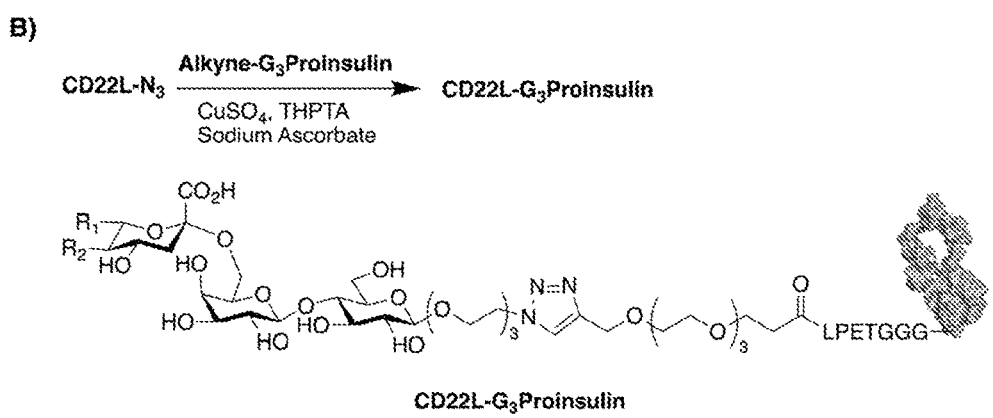
Figure 6C:
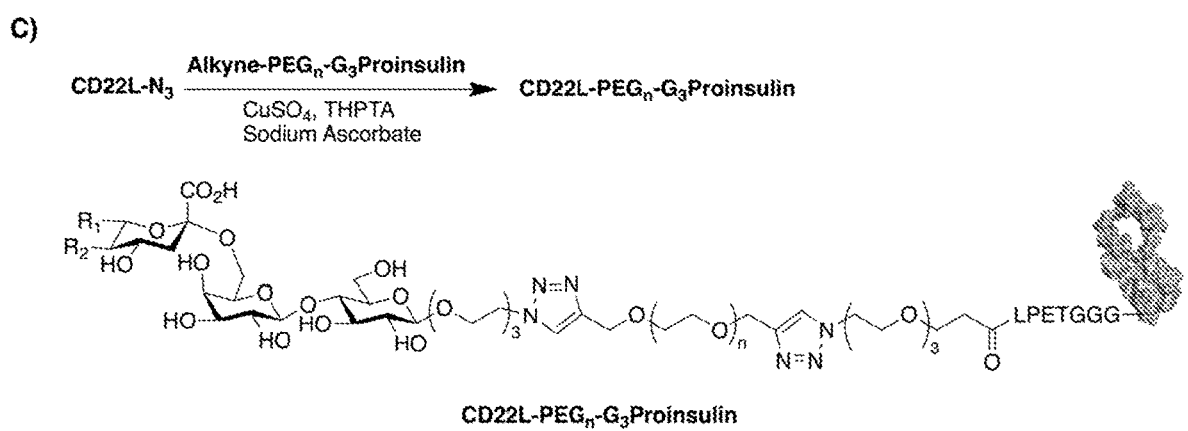

Additionally, the proinsulin-LPETG (SEQ ID NO: 11) variants will be ligated to a $G_3$-azide linker by eSrtA to give proinsulin-LPETG-$N_3$ (SEQ ID NO: 11) (FIG. 5C). $N_3$-$G_3$-proinsulin and proinsulin-LPETG-$N_3$ (SEQ ID NO: 11) will then be conjugated to alkyne-$PEG_n$-alkyne by CuAAC to give alkyne-$PEG_n$-$G_3$Proinsulin and alkyne-$PEG_n$-(proinsulinLPETG ("LPETG" disclosed as SEQ ID NO: 11)), respectively (FIGS. 5A, 5C). Proinsulin-CD22 L conjugates will be constructed in accordance with FIGS. 6B-6C.

Example 3: Determination of Insulin Variant Binding- to Anti-Insulin Antibody Binding kinetics were determined using bio-layer interferometry (BLI) in an Octet RED96e (ForteBio) according to the manufacturer's instructions. Monoclonal anti-insulin antibody (125 mAb) was loaded onto Anti-Mouse IgG Fc Capture Dip and Read Biosensors (ForteBio) at 40 μg/ml for 300 seconds, then equilibrated for 300 seconds in 1× kinetics buffer. The baseline was collected for 180 seconds in 1× kinetics buffer, association was performed for 300 seconds with each insulin variant at concentrations at 0.5 to 20× the estimated KD in 1× kinetics buffer, and dissociation was performed for 600 seconds in 1× kinetics buffer. Reference sensor and reference sample data was subtracted for each sample, and binding kinetics were calculated using a 1:1 global fit.

Figure 7:
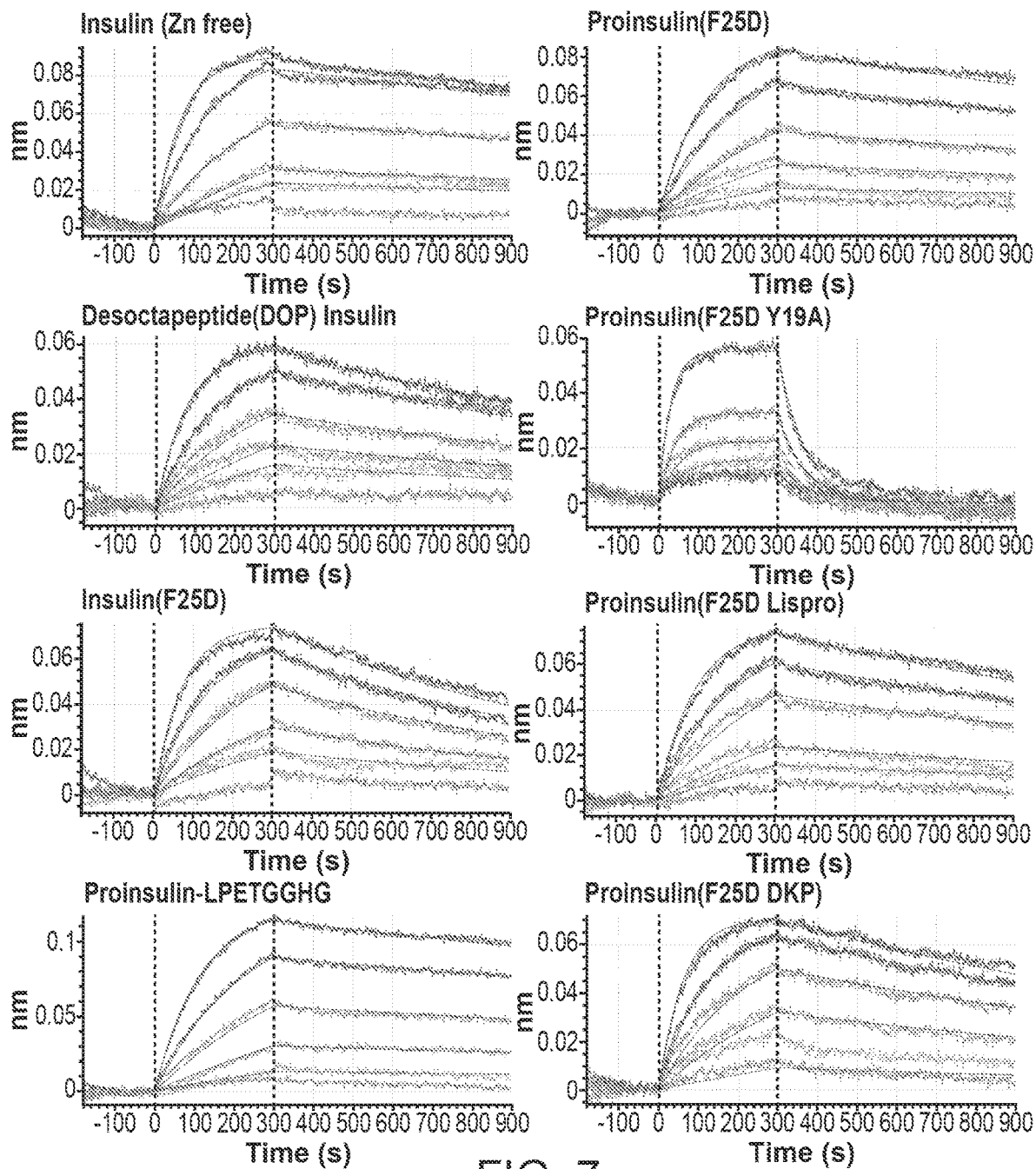
FIG. 7: Determination of Insulin Variant Binding to Anti-insulin Antibody. Binding kinetics data from bio-layer interferometry (BLI) of insulin variant binding with the anti-insulin antibody 125 mAb.

As shown in FIG. 7, most insulin variants possessed binding kinetics and affinities (<10 nM) similar to native human insulin. This demonstrates the ability of insulin variants to bind anti-insulin antibodies.

Figure 8:
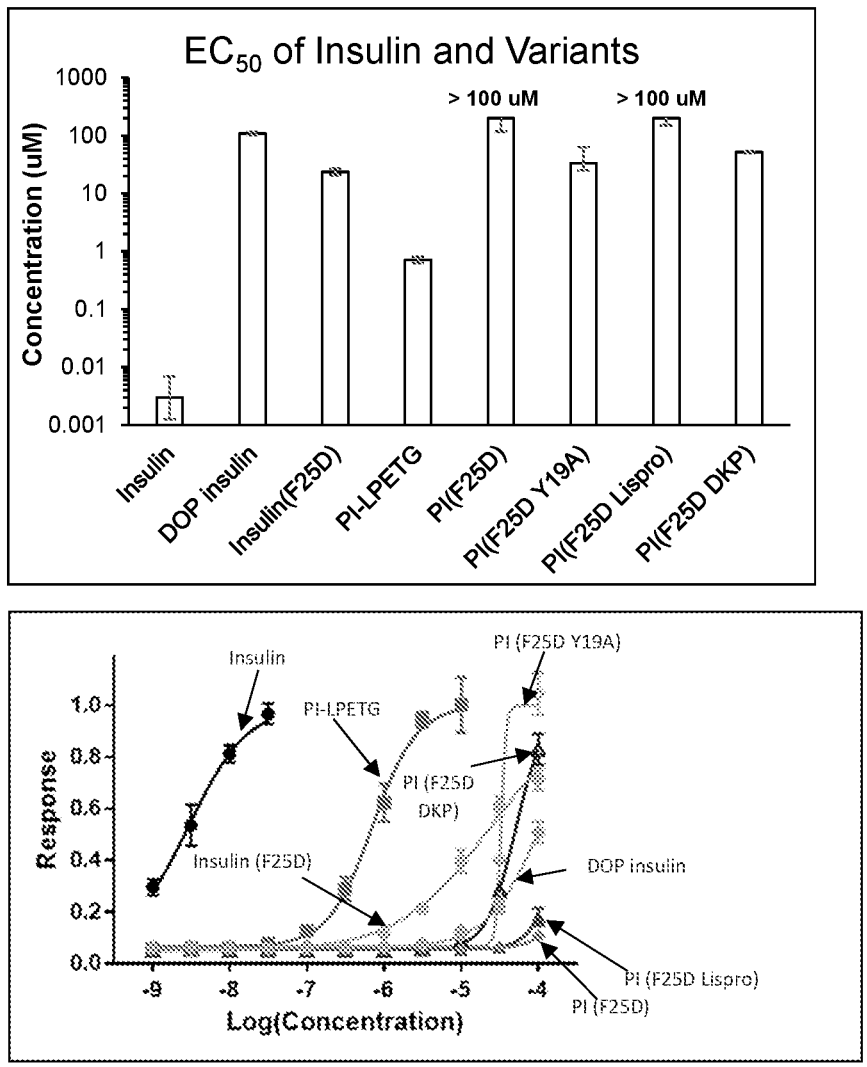
FIG. 8: Determination of Insulin Variant Hormonal Activity. Hormonal insulin receptor (CD220) activation data from a luciferase-reporter cell line.

Example 4: Functional Characterization of Insulin Variants

Determination of Insulin Variant Hormonal Activity. Insulin variants were incubated at concentrations of 1 nM to 100 μM with a human insulin receptor (hCD220) luciferase-reporter cell line (iLite Insulin Assay Ready Cells, Svar Life Science BM3060) according to the manufacturer's specifications in 96 well plates. Following incubation, the cells were equilibrated to room temperature and hCD220 signaling measured by luciferase luminescence using the Dual-Glo Luciferase Assay System (Promega) according to the manufacturer's specifications on a luminescence plate reader (Biotek Synergy H4 hybrid reader H4MLFPTAD). Firefly luciferase luminescence was standardized by subtracting background luminescence then dividing by background subtracted *Renilla* luciferase luminescence. EC50 values were calculated using non-linear regression analysis with variable slope and four parameters.

As shown in FIG. 8, the EC50 concentrations for insulin variants ranged from 240 to >40,000 times greater than that of native human insulin. This demonstrates the reduced ability of insulin variants to agonize the hormonal insulin receptor.

Conjugation of Insulin Variants to Functionalized Oligoglycines. A solution of 0.2 mM insulin variant, 0.8 mM GGG-PEG$_3$-azide, 0.02 mM pentamutant sortase A, 10 mM CaCl$_2$), and 0.4 mM NiSO4 in tris-buffered saline was stirred at room temperature for 2 hours. The reaction was quenched and acidified with 0.5% v/v 88% formic acid before the desired product was isolated by preparatory reverse phase liquid chromatography (Prep-LC) using a C18 stationary phase column with acidified (0.05% trifluoroacetic acid) water and acetonitrile as mobile phase. Rotational evaporation under reduced pressure was used to remove the acetonitrile before freezing and lyophilization to yield a white powder. An isolated yield of 80% with purity >95% was routinely achieved at 10+ mg scale. The product identity was confirmed by MALDI mass spectrometry.

Figure 9:
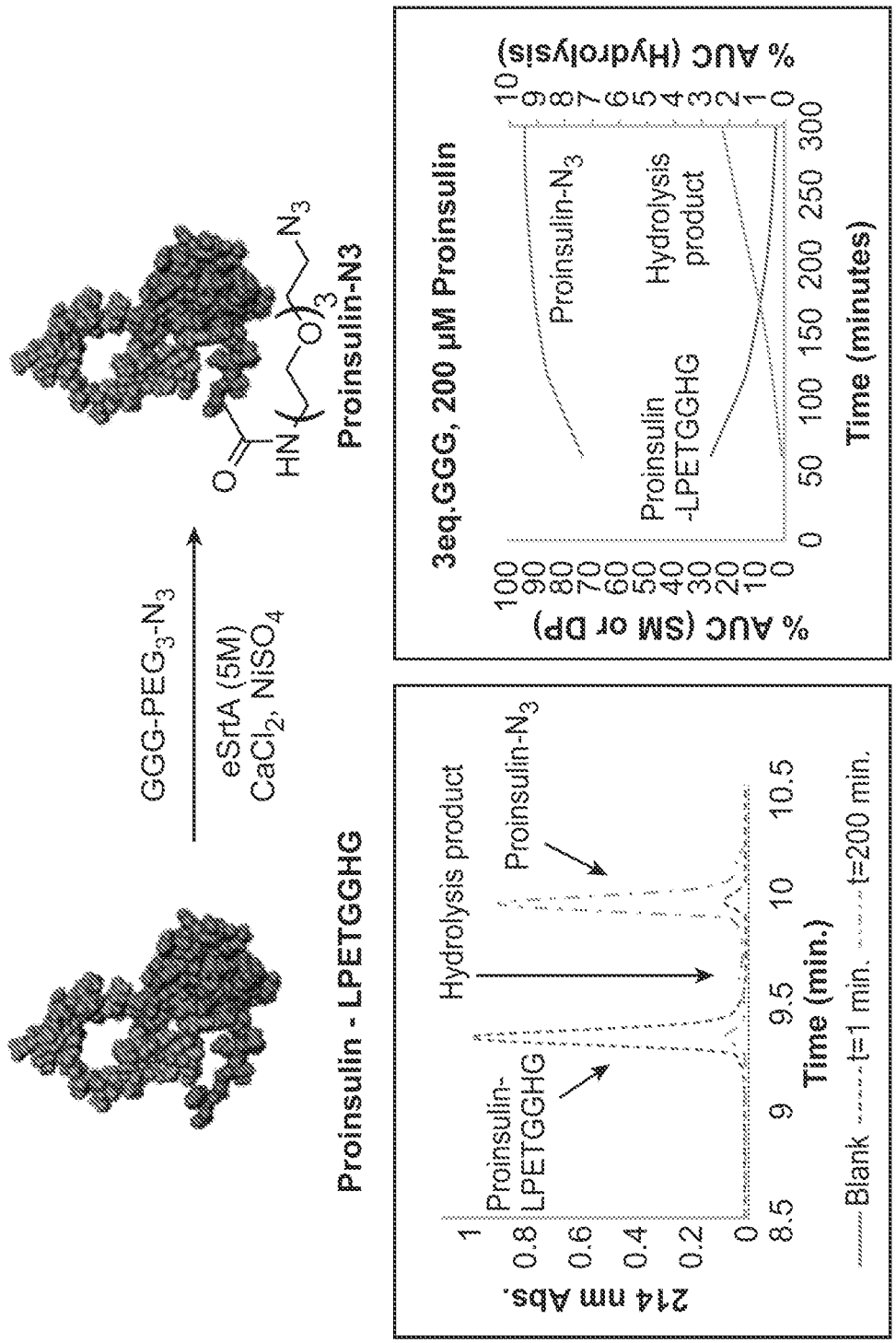
FIG. 9: Conjugation of Insulin Variants to Functionalized Oligoglycines. Site-selective conjugation of insulin variants to functionalized oligoglycines using sortase-mediated ligation for the synthesis of discrete multivalent conjugates.

FIG. 9 shows HPLC identification and quantification of sortase-mediated ligation yields over time.

Determination of 4-arm PEG-Insulin Binding to Anti-insulin Antibody. Binding kinetics were determined using bio-layer interferometry (BLI) in an Octet RED96e (ForteBio) according to the manufacturer's instructions. Monoclonal anti-insulin antibody (125 mAb) was loaded onto Anti-Mouse IgG Fc Capture Dip and Read Biosensors (ForteBio) at 10 µg/ml for 300 seconds then equilibrated for 300 seconds in 1× kinetics buffer. The baseline was collected for 180 seconds in 1× kinetics buffer, association was performed for 600 seconds with 4-arm PEG-insulin(1-4) at a concentration of 40 nM in 1× kinetics buffer, and dissociation was performed for 1800 seconds in 1× kinetics buffer. Reference sensor and reference sample data was subtracted for each sample, and binding kinetics were calculated using a 1:1 local fit.

Figure 10:
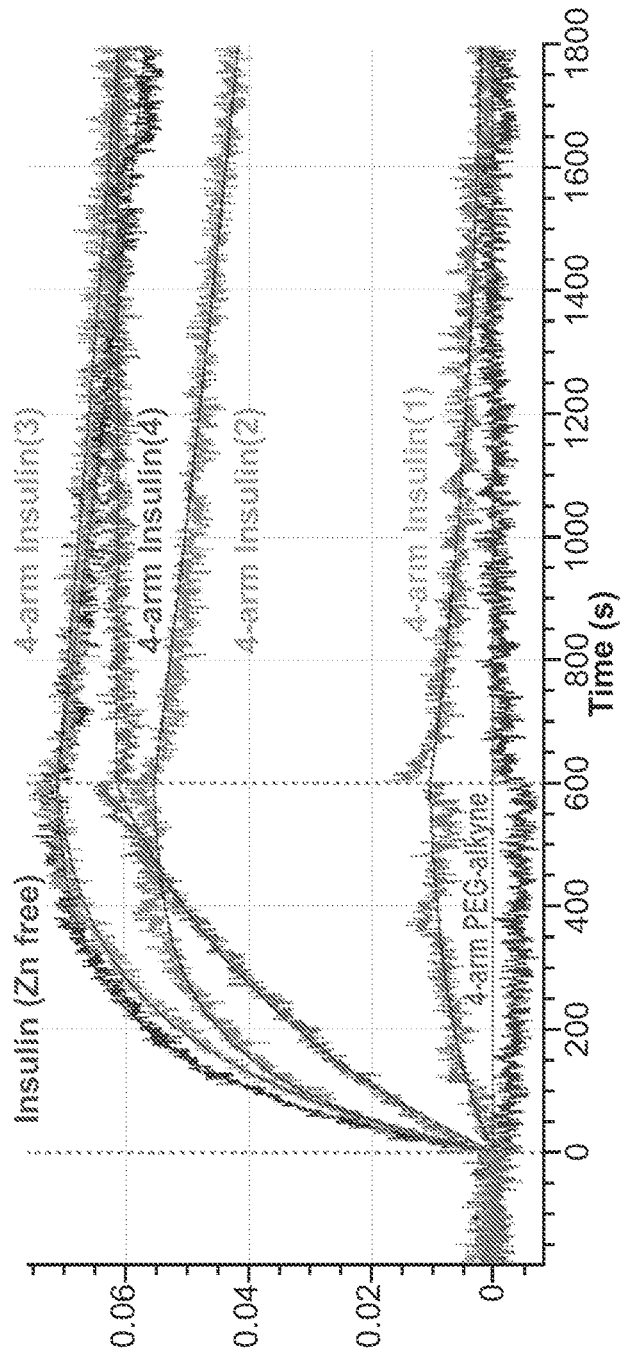
FIG. 10: Determination of 4-arm PEG-Insulin Binding to Anti-insulin Antibody. Binding kinetics data from bio-layer interferometry (BLI) of 4-arm PEG-insulin with 1-4 insulins conjugated to the 4-arm PEG scaffold.

FIG. 10 demonstrates the ability of 4-arm PEG-insulin with 2-4 insulins per scaffold to strongly bind the anti-insulin antibody 125 mAb and that increasing insulin valency increases binding affinity and decreases the dissociation rate as expected due to avidity.

Determination of Insulin Self-Association Within 4-arm PEG-Insulin. The status of insulin self-association within 4-arm PEG-insulin was determined using near-UV circular dichroism (near-UV CD) with a Jasco 1500 Circular Dichroism Spectrophotometer. Samples were dissolved at insulin concentrations of 0.6 and 0.06 mM in sodium phosphate buffer pH 7.4 with cell path lengths of 1 and 10 mm, respectively. Samples with zinc contained 0.4 molar equivalents of zinc sulfate per insulin. CD spectra were recorded from 250 to 310 nm, and the results of triplicate measurements were averaged. The near-UV CD temperature melt was performed from 20 to 90° C. at 274 nm with samples at 0.6 mM in 1 mm pathlength cuvettes.

Figure 11:
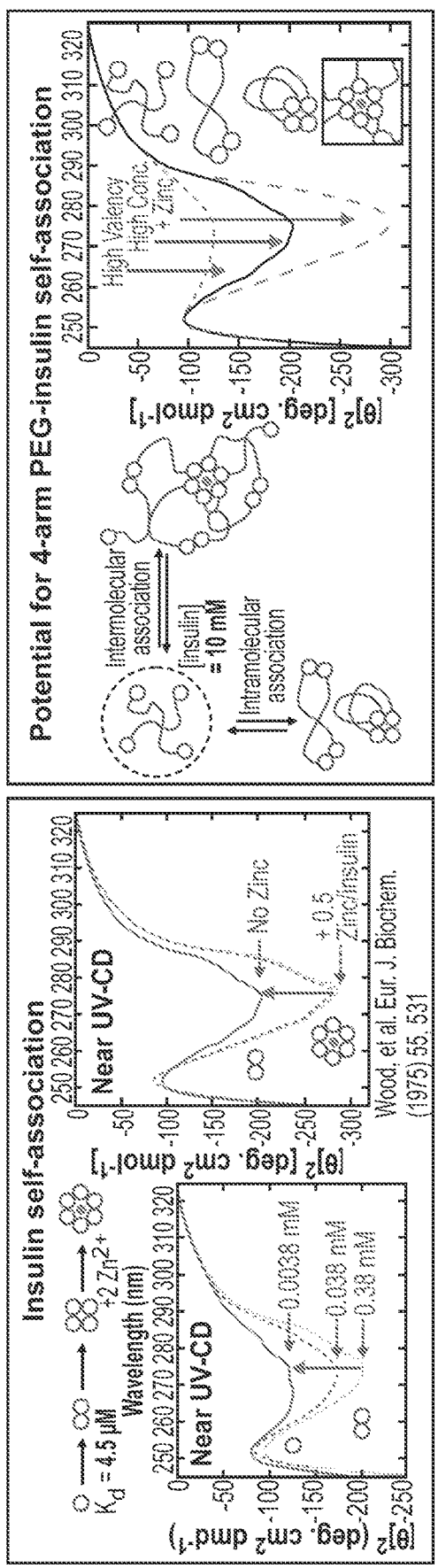
FIG. 11: Determination of Insulin Self-Association Within 4-arm PEG-Insulin. (Top) Depiction of the effect of insulin self-association on near-UV circular dichroism (CD) spectra and the potential for self-association of 4-arm PEG-insulin(4). (Bottom) Near-UV CD data for insulin, synthetic intermediates, 4-arm PEG-insulin(1), and 4-arm PEG-insulin(4).
Figure 11:
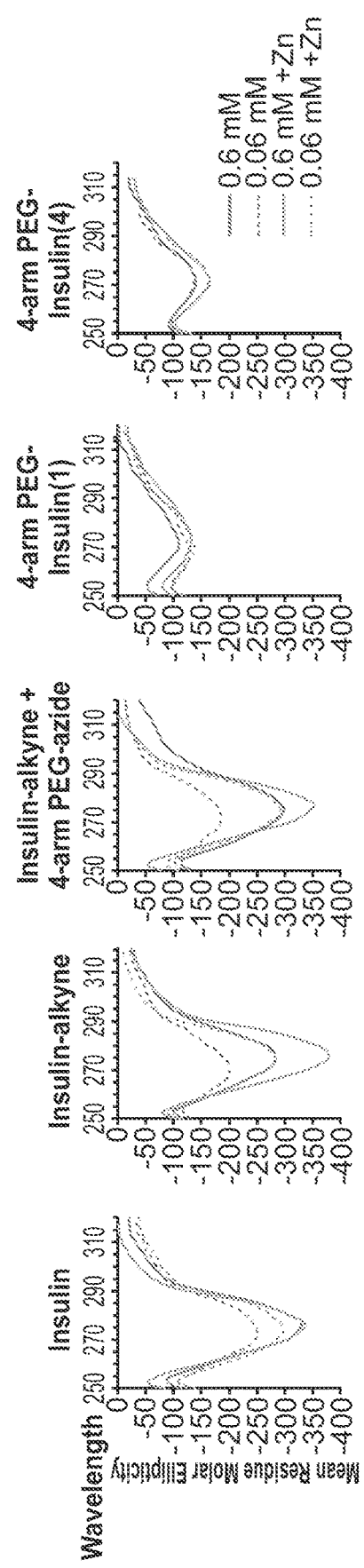
Figure 11:
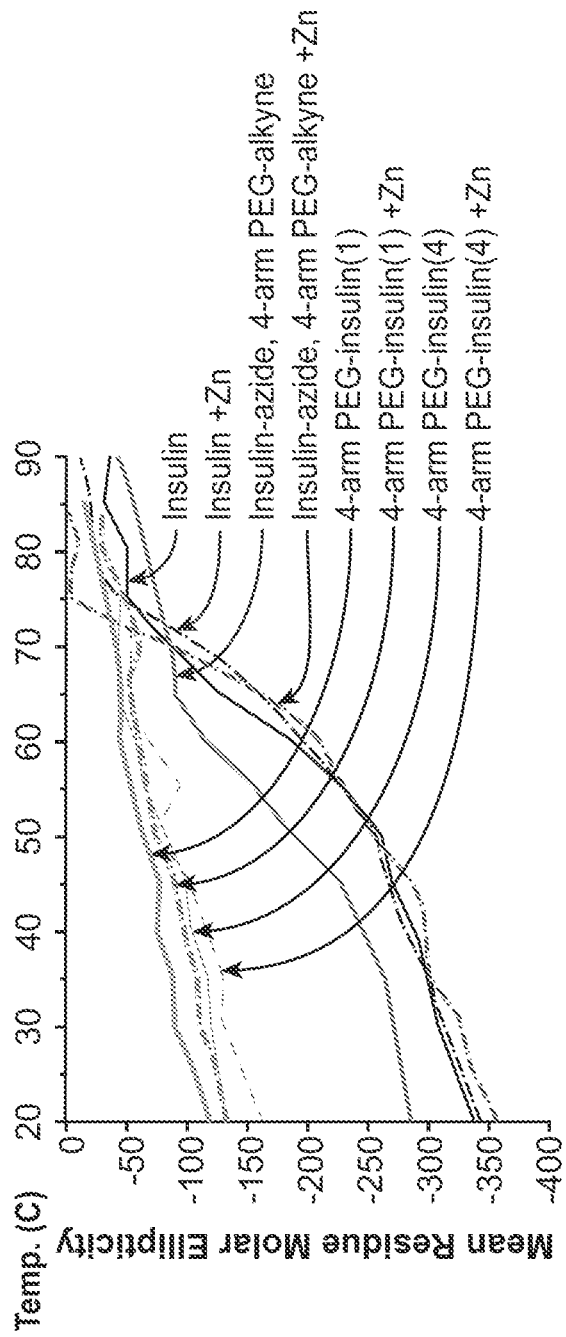

FIG. 11 demonstrates that 4-arm PEG-insulin minimally self-associates intramolecularly and does not self-associate intermolecularly.

Determination of Insulin Variant and 4-arm PEG-Insulin Variant Hydrodynamic Radii. The hydrodynamic radius of insulin variants and 4-arm PEG-insulin variant conjugates was determined using dynamic light scattering (DLS) on a Zetasizer Nano ZS (Malvern). Insulin variants were dissolved at 0.6 mM and 4-arm PEG-insulin variant conjugates were dissolved at 25 µM in tris-buffered saline then filtered through 0.22 m PVDF filters. The results of triplicate measurements were averaged.

Figure 12:
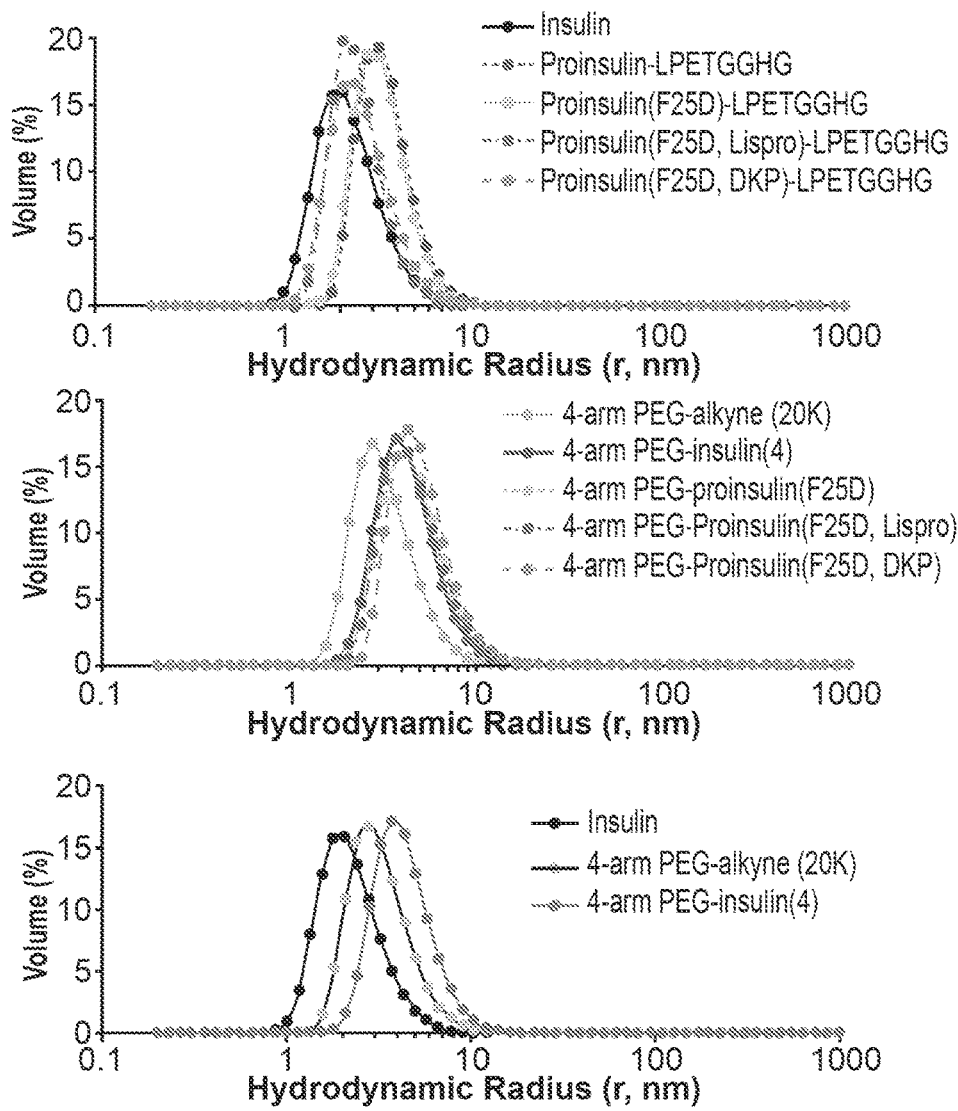
FIG. 12: Determination of Insulin Variant and 4-arm PEG-Insulin Variant Hydrodynamic Radii. Hydrodynamic radii data from dynamic light scattering of insulin variants and 4-arm PEG-insulin variants.

FIG. 12 demonstrates insulin variants with Lispro and DKP mutations exist as lower-oligomeric species in solution, that 4-arm PEG-insulin variant conjugates do not self-associate intermolecularly, and that 4-arm PEG-insulin variant conjugates possess favorable hydrodynamic radii.

Determination of Insulin Variant and 4-arm PEG-Insulin Variant Secondary Structure. The secondary structure of insulin variants and 4-arm PEG-insulin variant conjugates was determined using far-UV circular dichroism (far-UV CD) with a Jasco 1500 Circular Dichroism Spectrophotometer. Samples were dissolved at insulin concentrations of 0.2 mg/ml in sodium phosphate buffer pH 7.4 with cell path lengths of 1 mm. CD spectra were recorded from 190 to 260 nm, and the results of triplicate measurements were averaged. Percent alpha-helical character was calculated using the BeStSeL online server.

Figure 13:
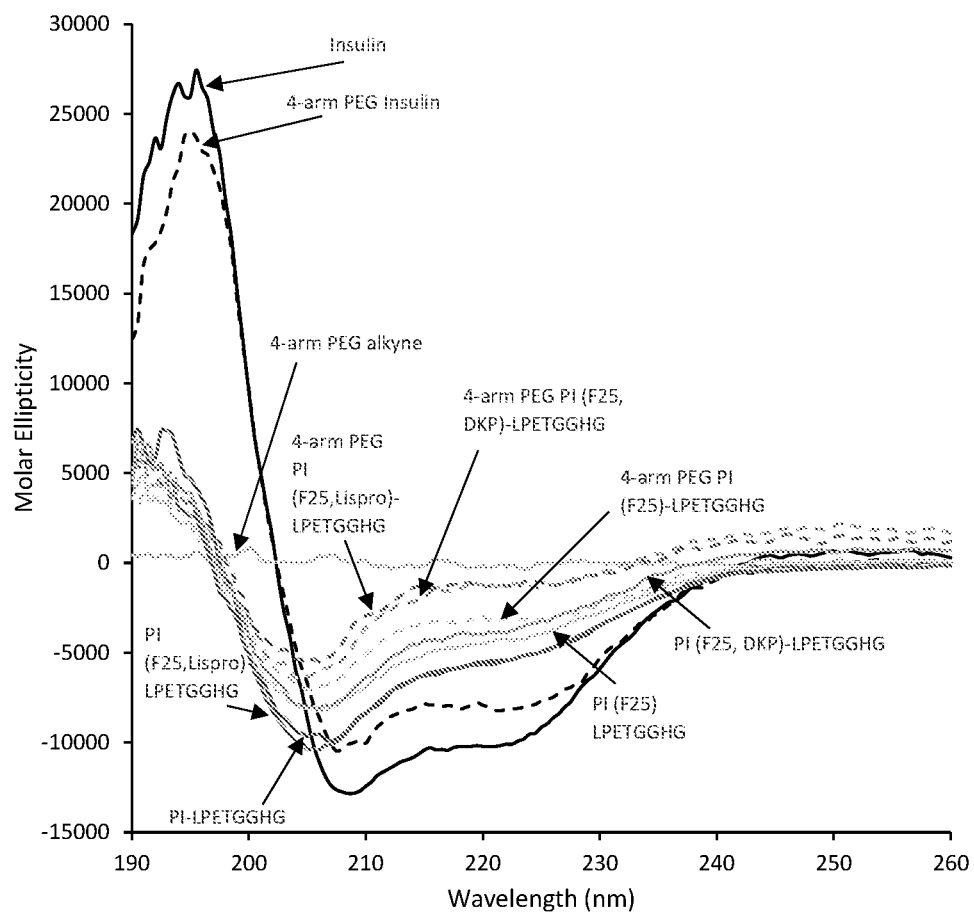
FIG. 13: Determination of Insulin Variant and 4-arm PEG-Insulin Variant Secondary Structure. Secondary structure data from far-UV circular dichroism (CD) of insulin variants and 4-arm PEG-insulin variants.

FIG. 13 demonstrates the expected reduction in alpha-helical character for insulin variants retaining the primarily disordered proinsulin C-peptide and the retention of insulin variant secondary structure when conjugated to 4-arm PEG.

Determination of Insulin Variant and 4-arm PEG-Insulin Variant Size Heterogeneity. The heterogeneity of insulin variants and 4-arm PEG-insulin variant conjugates was determined using size-exclusion chromatography with a Superdex 200 Increase HiScale 16/40 (GE) column in tris-buffered saline. Fifty µl samples with concentrations of 0.5-2 mg/ml were injected, and the data is representative of triplicate measurements.

Figure 14:
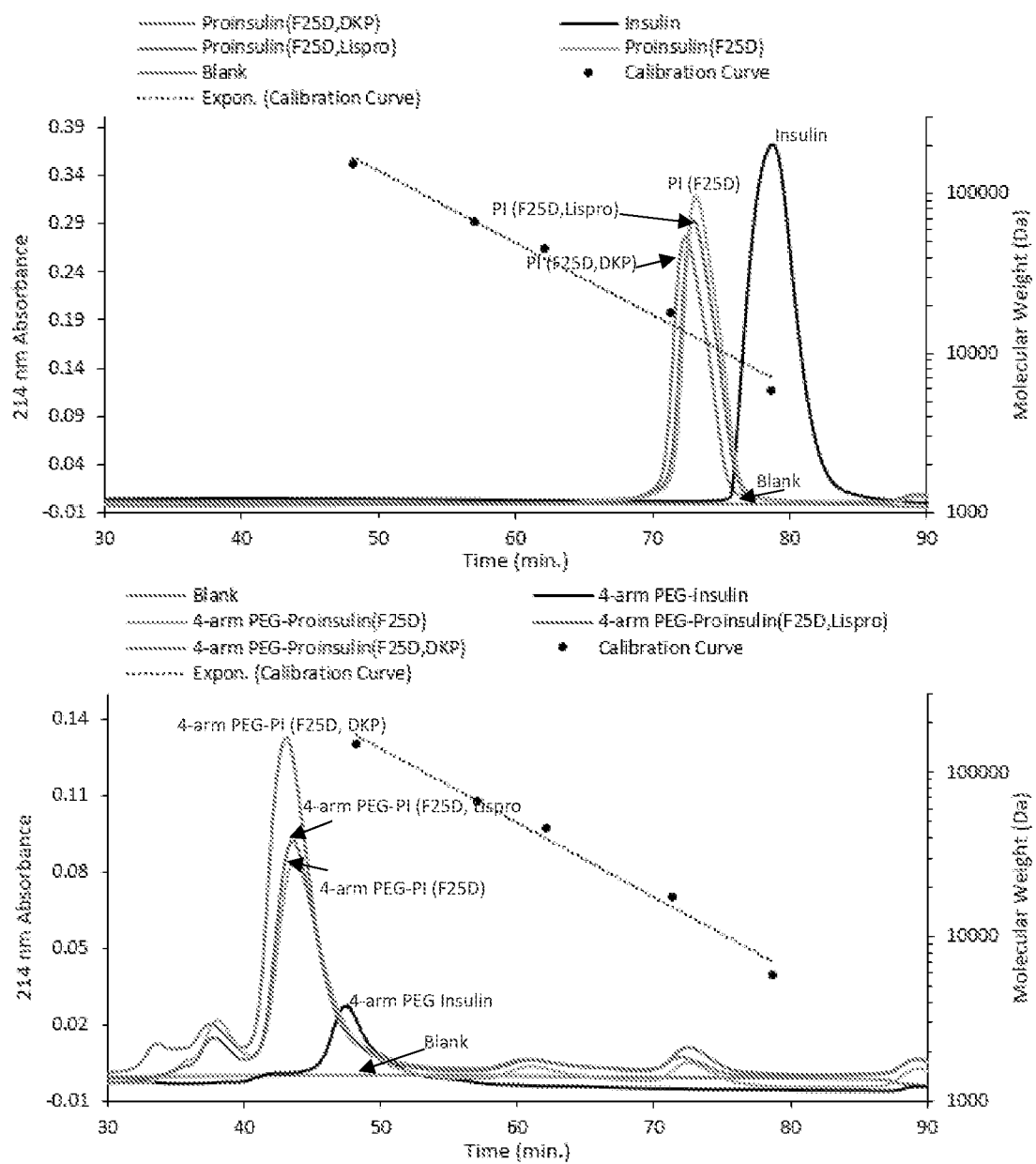
FIG. 14: Determination of Insulin Variant and 4-arm PEG-Insulin Variant Size and Heterogeneity. Molecular weight estimation and heterogeneity data from size exclusion chromatography (SEC) for insulin variants and 4-arm PEG-insulin variant conjugates.

FIG. 14 demonstrates the size distribution of 4-arm PEG-insulin variant species following HPLC purification and estimates their hydrodynamic radius to be similar to a 200-300 kDa protein.

Determination of Insulin Variant Binding to Anti-Insulin B cells. VH125 non obese diabetic mice splenocytes containing 1-3% insulin-specific B cells were incubated with FITC-labeled insulin variants at 2 µM and co-labeled with Alexa Fluor 647 anti-mouse CD19 antibody and PI/cyanine7 anti-mouse CD3 antibody for 30 minutes at 4° C. Samples were washed then analyzed by flow cytometry (BD FACSFusion). Splenocytes were gated based on CD19 and CD3 expression and FITC signal. Insulin variant binding was compared to native human insulin binding for specific interactions with insulin-specific B cells (FITC$^{Hi}$) and for non-specific interactions with B and T cells (FITC$^{Lo}$)

Figure 15:
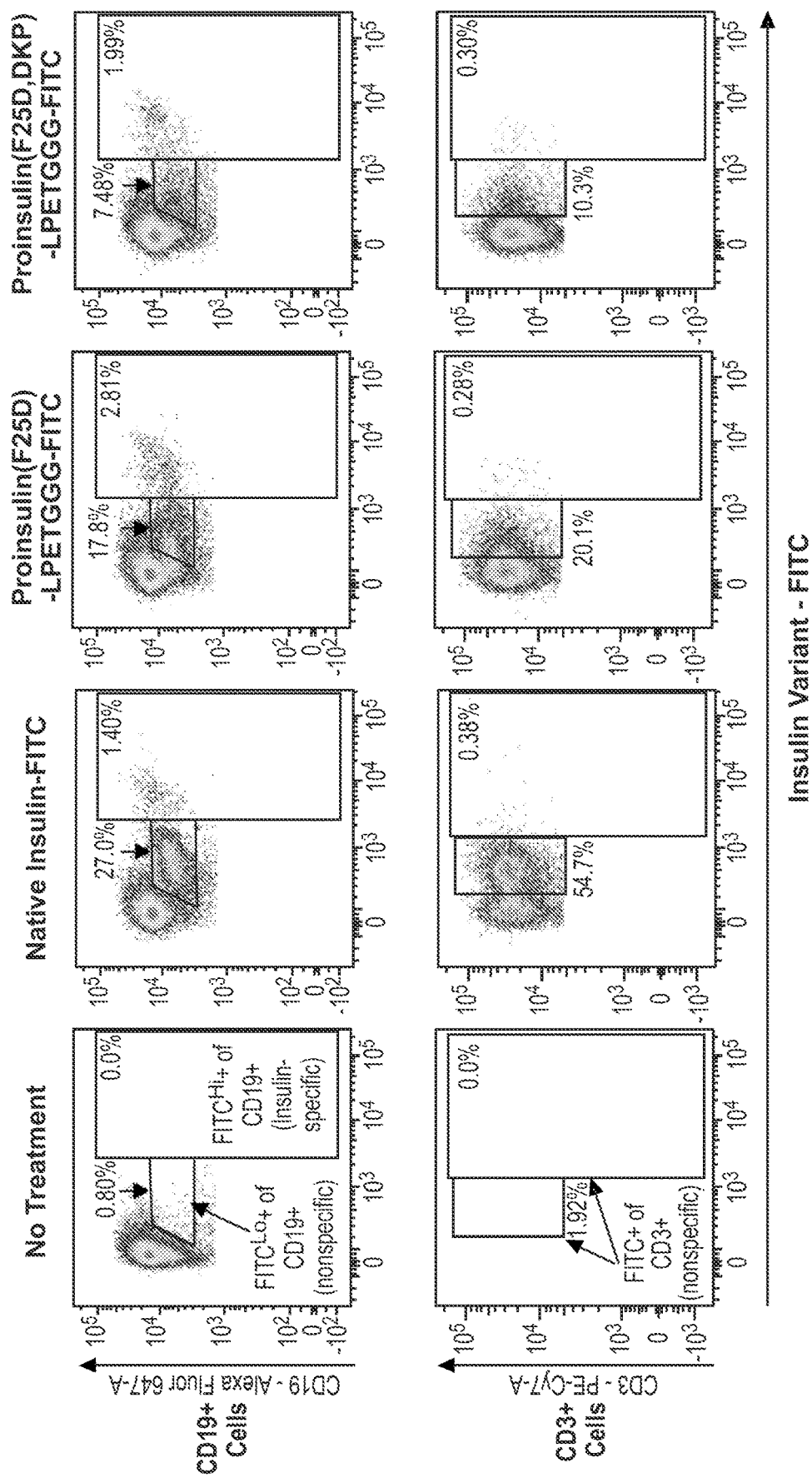
FIG. 15: Determination of Insulin Variant Binding to Anti-Insulin B cells. Anti-insulin VH125 non-obese diabetic mouse splenocytes binding data from flow cytometry for insulin variants labeled with FITC by site-selective sortase mediated ligation.
Figure 15:
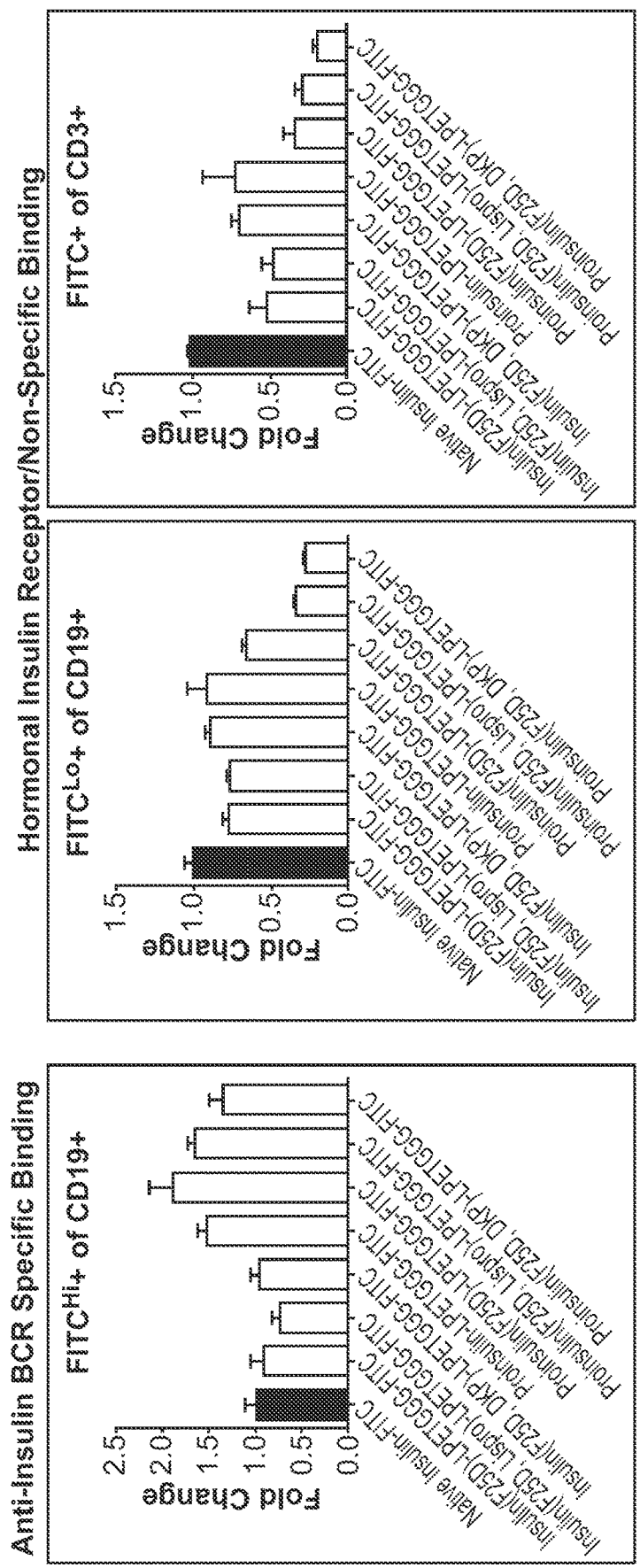

FIG. 15 demonstrates the improved selectivity of insulin variants to bind insulin-specific B cells (FITC$^{Hi}$ of CD19+) over non-insulin specific B cells (FITC$^{Lo}$ of CD19+) or T cells (FITC$^+$ of CD3+) even at high concentrations (2 µM).

Example 5: Effects of 4-Arm PEG-Insulin Variants of the Present Technology on Anti-Insulin B Cells Determination of 4-arm PEG-insulin Variant Binding to Anti-Insulin B cells. 125Tg non obese diabetic mice splenocytes containing >90% insulin-specific B cells are incubated with FITC-labeled 4-arm PEG-insulin variant at 2 µM and co-labeled with Alexa Fluor 647 anti-mouse CD19 antibody and PI/cyanine7 anti-mouse CD3 antibody for 30 minutes at 4° C. Samples are washed then analyzed by flow cytometry. Splenocytes are gated based on CD19 and CD3 expression and FITC signal. 4-arm PEG-insulin variant binding is compared to native human insulin binding for specific interactions with insulin-specific B cells and for non-specific interactions with T cells (Apley et. al. J. Vis. Exp. 2020, 164, e61827).

It is anticipated that the 4-arm PEG-insulin variants will exhibit strong binding kinetics and affinities to insulin-specific B cells, and little to no non-specific interactions with T cells.

Determination of 4-arm PEG-insulin variant prevention of B cell activation in Vitro. Splenocytes isolated from 125Tg non-obese diabetic (NOD) mice are incubated with treatment (4-arm PEG-insulin variant or 4-arm PEG-insulin variant/CD22L) and are challenged with anti-IgM Fab2', CpG, or anti-CD40/IL2 (Acevedo-Suarez et. al. *J Immunol* 2005, 174, 827). Splenocytes will be analyzed by flow cytometry and B cell expression of CD86 will be quantified along with B cell proliferation by CellTrace Violet. Additionally, cytokine secretion will be analyzed by ELISA for IFN-gamma, TNF-alpha, IL-2, IL-17A, IL-6, and IL-10 (Johnson et. al. *ACS Appl. Bio. Mater.* 2020, 3, 6319).

It is anticipated that the 4-arm PEG-insulin variant or 4-arm PEG-insulin variant/CD22 L conjugate will effectively prevent in vitro B cell activation compared to untreated controls.

Protection against disease onset in non-obese diabetic mice. Non obese diabetic (NOD) mice and VH125 NOD mice are treated weekly with a subcutaneous injection of 0.2-1.0 mg 4-arm PEG-insulin variant or 4-arm PEG-insulin variant/CD22 L and monitored for onset of type 1 diabetes with two consecutive measurements of blood glucose >200 mg/dL (Henry et. al. *Diabetes* 2012, 61, 2037).

It is anticipated that the 4-arm PEG-insulin variant or 4-arm PEG-insulin variant/CD22 L conjugate will effectively protect against disease onset in non-obese diabetic mice compared to untreated controls.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A conjugate of Formula I (I)

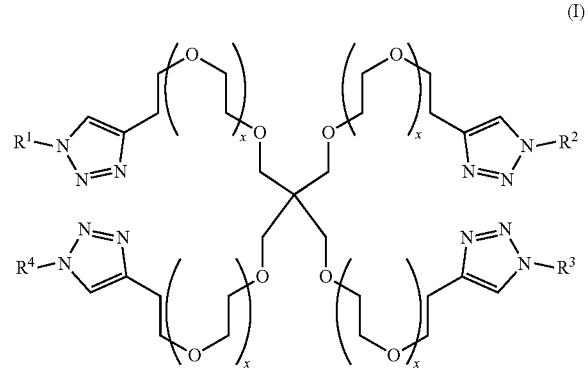

or a pharmaceutically acceptable salt and/or solvate thereof, wherein $R^1$, $R^2$, $R^3$, and $R^4$ are each independently

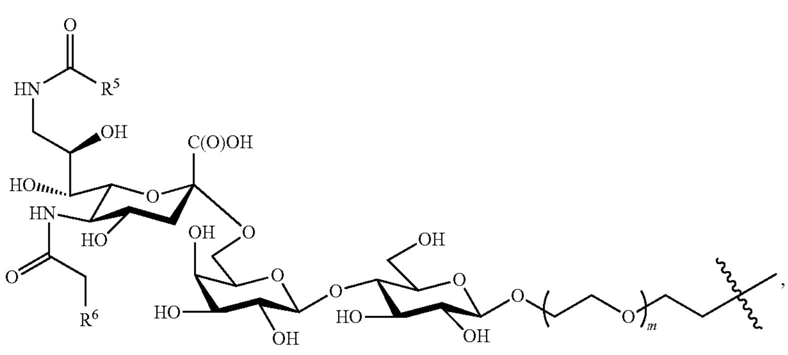

,

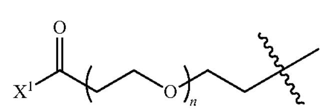

, or

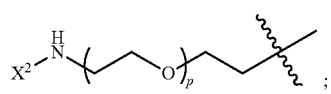

R[5] is independently at each occurrence aryl or aralkyl;
R[6] is independently at each occurrence halo, hydroxyl, aryl, or heteroaryl;
X[1] is independently at each occurrence a F-nitrogen atom of lysine of SEQ ID NO: 2 or a substitution variant thereof of a first proinsulin polypeptide;
X[2] is independently at each occurrence a carbonyl carbon of a nitrogen atom of a C-terminal glycine of a sortase moiety wherein the sortase moiety is fused to a second proinsulin polypeptide a C-terminus of the second proinsulin polypeptide;
x is independently at each occurrence 0, 1, 2, 3, 4, 5, 6, 7, 8, 9, 10, 11, or 12;
m is independently at each occurrence 0, 1, 2, 3, 4, 5, 6, 7, 8, 9, 10, 11, or 12;
n is independently at each occurrence 0, 1, 2, 3, 4, 5, 6, 7, 8, 9, 10, 11, or 12; and
p is independently at each occurrence 0, 1, 2, 3, 4, 5, 6, 7, 8, 9, 10, 11, or 12.

B. The conjugate of Paragraph A, wherein the conjugate has a volume-weighted average diameter as determined by dynamic light scattering of about 2 nm to about 15 nm.

C. The conjugate of Paragraph A or Paragraph B, wherein the conjugate has a volume-weighted average hydrodynamic diameter as determined by dynamic light scattering of about 4 nm to about 8 nm.

D. The conjugate of any one of Paragraphs A-C, wherein the conjugate has a number-average molecular weight of about 10,000 to about 150,000.

E. The conjugate of any one of Paragraphs A-D, wherein the conjugate has a number-average molecular weight of about 40,000 to about 80,000.

F. The conjugate of any one of Paragraphs A-E, wherein R[6] is independently at each occurrence halo or hydroxyl.

G. The conjugate of any one of Paragraphs A-F, wherein R[5] is independently at each occurrence

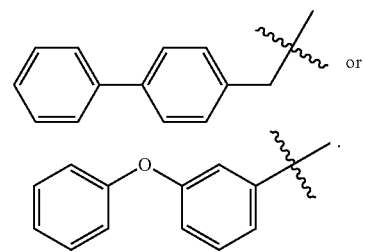

H. The conjugate of any one of Paragraphs A-G, wherein the first proinsulin polypeptide is fused to a sortase moiety, wherein the first proinsulin polypeptide includes an insulin B-chain of SEQ ID NO: 2, an insulin C-chain of SEQ ID NO: 3, and an insulin A-chain of SEQ ID NO: 4.

I. The conjugate of Paragraph H, wherein the sortase moiety is located at the N-terminus or the C-terminus of the first proinsulin polypeptide.

J. The conjugate of any one of Paragraphs A-I, wherein the sequence of the sortase moiety is SEQ ID NO: 6.

K. The conjugate of any one of Paragraphs A-J, wherein the first proinsulin polypeptide comprises a F25D substitution in the insulin B-chain of SEQ ID NO: 2 and/or a Y19A or Y19 L substitution in an insulin A-chain of SEQ ID NO: 4.

L. The conjugate of any one of Paragraphs A-K, wherein the first proinsulin polypeptide comprises a H10D substitution in the insulin B-chain of SEQ ID NO: 2.

M. The conjugate of any one of Paragraphs A-L, wherein the first proinsulin polypeptide comprises both P28K and K29P substitutions in the insulin B-chain of SEQ ID NO: 2

N. The conjugate of any one of Paragraphs A-M, wherein the first proinsulin polypeptide comprises P28K, K29P, and H10D substitutions in the insulin B-chain of SEQ ID NO: 2.

O. The conjugate of any one of Paragraphs A-N, wherein the first proinsulin polypeptide comprises a signal peptide sequence.

P. The conjugate of Paragraph O, wherein the signal peptide sequence is a native or engineered signal peptide sequence.

Q. The conjugate of Paragraph O or Paragraph P, wherein the signal peptide sequence is SEQ ID NO: 5.

R. The conjugate of any one of Paragraphs A-Q, wherein the second proinsulin polypeptide comprises a F25D substitution in an insulin B-chain of SEQ ID NO: 2 and/or a Y19A or Y19 L substitution in an insulin A-chain of SEQ ID NO: 4.

S. The conjugate of any one of Paragraphs A-R, wherein the second proinsulin polypeptide comprises a H10D substitution in an insulin B-chain of SEQ ID NO: 2.

T. The conjugate of any one of Paragraphs A-S, wherein the second proinsulin polypeptide comprises both P28K and K29P substitutions in an insulin B-chain of SEQ ID NO: 2

U. The conjugate of any one of Paragraphs A-T, wherein the second proinsulin polypeptide comprises P28K, K29P, and H10D substitutions in an insulin B-chain of SEQ ID NO: 2.

V. The conjugate of any one of Paragraphs A-U, wherein the second proinsulin polypeptide comprises a signal peptide sequence.

W. The conjugate of Paragraph V, wherein the signal peptide sequence is a native or engineered signal peptide sequence.

X. The conjugate of Paragraph V or Paragraph W, wherein the signal peptide sequence is SEQ ID NO: 5.

Y. The conjugate of any one of Paragraphs A-X, wherein the first proinsulin polypeptide and/or the second proinsulin polypeptide comprise an amino acid sequence selected from the group consisting of SEQ ID NOs: 8-10.

Z. The conjugate of any one of Paragraphs A-Y, wherein the first proinsulin polypeptide and the second proinsulin polypeptide exhibit reduced activation of hormonal insulin receptor (IR) relative to native human insulin.

AA. A composition comprising a conjugate of any one of Paragraphs A-Z and a pharmaceutically acceptable carrier.

AB. A pharmaceutical composition comprising a pharmaceutically acceptable carrier and an effective amount of a compound of any one of Paragraphs A-Z.

AC. The pharmaceutical composition of Paragraph AB, wherein the effective amount of the compound is effective to treat one or more of Type 1 diabetes, juvenile diabetes, insulin-dependent diabetes, or latent autoimmune diabetes in a subject.

AD. The pharmaceutical composition of Paragraph AC, wherein the subject is not hyperglycemic.

AE. The pharmaceutical composition of Paragraph AC or Paragraph AD, wherein the subject has detectable levels of an insulin autoantibody (IAA).

AF. The pharmaceutical composition of any one of Paragraphs AC-AE, wherein the subject has detectable levels of an insulin-specific B cell population.

AG. The pharmaceutical composition of any one of Paragraphs AC-AF, wherein the subject harbors one or more human leukocyte antigen (HLA) haplotypes selected from the group consisting of: (a) DRB1*0301-DQA1*0501-DQB1*0201; (b) DRB1*0405-DQA1*0301-DQB1*0302; (c) DRB1*0401-DQA1*0301-DQB*0302; (d) DRB1*0402-DQA1*0301-DQB1*0302; (e) DRB1*0404-DQA1*0301-DQB1*0302; and (f) DRB1*0801-DQB1*0401-DQB1*0402.

AH. The pharmaceutical composition of any one of Paragraphs AB-AG, wherein the pharmaceutical composition is formulated for parenteral administration, intravenous administration, or subcutaneous administration.

AI. A kit comprising the conjugate of any one of Paragraphs A-Z, and instructions for use.

AJ. A method for treating or preventing autoimmune diabetes in a subject in need thereof comprising administering to the subject an effective amount of the conjugate of any of Paragraphs A-Z.

AK. The method of Paragraph AJ wherein autoimmune diabetes comprises Type 1 diabetes, juvenile diabetes, insulin-dependent diabetes, or latent autoimmune diabetes.

AL. The method of Paragraph AJ or Paragraph AK, wherein the subject has been diagnosed with or is at risk for autoimmune diabetes.

AM. The method of any one of Paragraphs AJ-AL, wherein the subject is not hyperglycemic.

AN. The method of any one of Paragraphs AJ-AM, wherein the subject has detectable levels of an insulin autoantibody (IAA).

AO. The method of any one of Paragraphs AJ-AN, wherein the subject has detectable levels of an insulin-specific B cell population.

AP. The method of any one of Paragraphs AJ-AO, wherein the subject harbors one or more human leukocyte antigen (HLA) haplotypes selected from the group consisting of: (a) DRB1*0301-DQA1*0501-DQB1*0201; (b) DRB1*0405-DQA1*0301-DQB1*0302; (c) DRB1*0401-DQA1*0301-DQB*0302; (d) DRB1*0402-DQA1*0301-DQB1*0302; (e) DRB1*0404-DQA1*0301-DQB1*0302; and (f) DRB1*0801-DQB1*0401-DQB1*0402.

AQ. The method of any one of Paragraphs AJ-AP, wherein the conjugate is administered parenterally, intravenously or subcutaneously.

AR. The method of any one of Paragraphs AJ-AQ, wherein administration of the conjugate induces anergy in insulin-binding B cells in the subject.

AS. The method of any one of Paragraphs AJ-AR, wherein blood glucose levels of the subject after at least one administration of the conjugate are comparable to that observed in the subject prior to the at least one administration.

AT. The method of any one of Paragraphs AJ-AS, wherein the subject is a child or adult.

Other embodiments are set forth in the following claims, along with the full scope of equivalents to which such claims are entitled.

What is claimed is:

1. A conjugate of Formula I

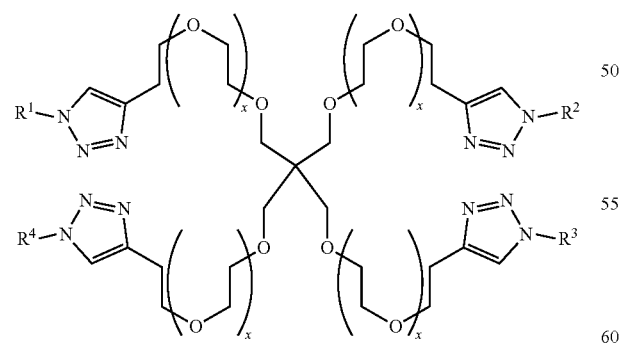

or a pharmaceutically acceptable salt and/or solvate thereof, wherein $R^1$, $R^2$, $R^3$ and $R^4$ are each independently

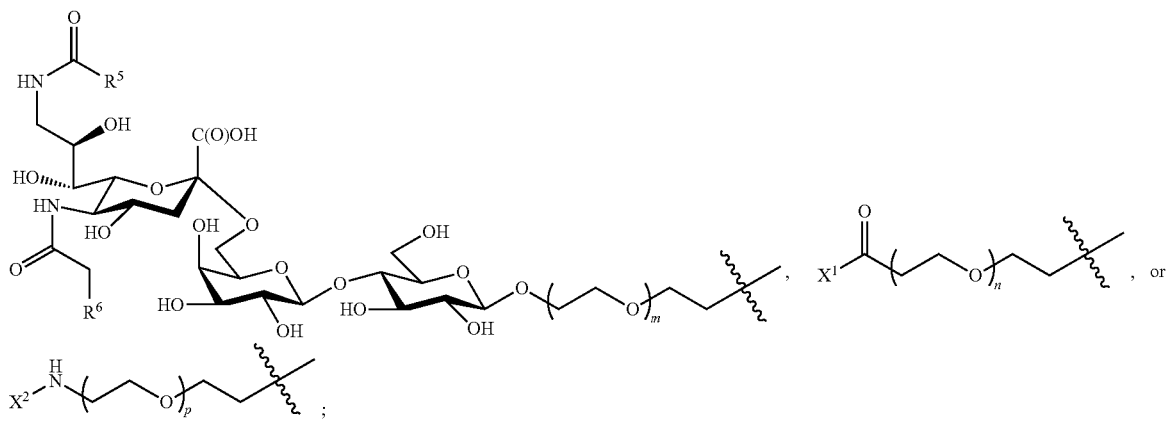

$R^5$ is independently at each occurrence aryl or aralkyl;
$R^6$ is independently at each occurrence halo, hydroxyl, aryl, or heteroaryl;
X1 is independently at each occurrence a s-nitrogen atom of lysine of SEQ ID NO: 2 or a substitution variant thereof of a first proinsulin polypeptide;
X2 is independently at each occurrence a carbonyl carbon or a nitrogen atom of a C-terminal glycine of a sortase moiety wherein the sortase moiety is fused to a second proinsulin polypeptide at the C-terminus of the second proinsulin polypeptide;
x is independently at each occurrence 0, 1, 2, 3, 4, 5, 6, 7, 8, 9, 10, 11, or 12;
m is independently at each occurrence 0, 1, 2, 3, 4, 5, 6, 7, 8, 9, 10, 11, or 12;
n is independently at each occurrence 0, 1, 2, 3, 4, 5, 6, 7, 8, 9, 10, 11, or 12; and
p is independently at each occurrence 0, 1, 2, 3, 4, 5, 6, 7, 8, 9, 10, 11, or 12,
optionally wherein the sequence of the sortase moiety is SEQ ID NO: 6.

2. The conjugate of claim 1, wherein the conjugate has a volume-weighted average diameter as determined by dynamic light scattering of about 2 nm to about 15 nm or
wherein the conjugate has a volume-weighted average hydrodynamic diameter as determined by dynamic light scattering of about 4 nm to about 8 nm; or
wherein the conjugate has a number-average molecular weight of about 10,000 to about 150,000 or about 40,000 to about 80,000.

3. The conjugate of claim 1, wherein $R^5$ is independently at each occurrence

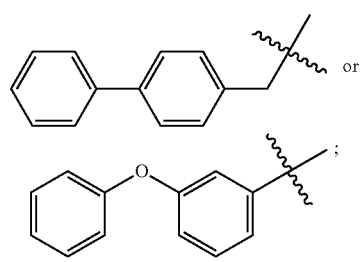

wherein $R^6$ is independently at each occurrence halo or hydroxyl.

4. The conjugate of claim 1, wherein the first proinsulin polypeptide is fused to a sortase moiety, wherein the first proinsulin polypeptide includes an insulin B-chain of SEQ ID NO: 2, an insulin C-chain of SEQ ID NO: 3, and an insulin A-chain of SEQ ID NO:4, optionally wherein the sortase moiety is located at the N-terminus or the C-terminus of the first proinsulin polypeptide.

5. The conjugate of claim 1, wherein the first proinsulin polypeptide comprises a F25D substitution in the insulin B-chain of SEQ ID NO: 2 and/or a Y19A or Y19 L substitution in an insulin A-chain of SEQ ID NO: 4; or
wherein the first proinsulin polypeptide comprises a H10D substitution in the insulin B-chain of SEQ ID NO: 2; or
wherein the first proinsulin polypeptide comprises both P28K and K29P substitutions in the insulin B-chain of SEQ ID NO: 2; or
wherein the first proinsulin polypeptide comprises P28K, K29P, and H10D substitutions in the insulin B-chain of SEQ ID NO: 2.

6. The conjugate of claim 1, wherein the first proinsulin polypeptide comprises a signal peptide sequence, optionally wherein the signal peptide sequence is a native or engineered signal peptide sequence or wherein the signal peptide sequence is SEQ ID NO: 5.

7. The conjugate of claim 1, wherein the second proinsulin polypeptide comprises a F25D substitution in an insulin B-chain of SEQ ID NO: 2 and/or a Y19A or Y19 L substitution in an insulin A-chain of SEQ ID NO: 4; or
wherein the second proinsulin polypeptide comprises a H10D substitution in an insulin B-chain of SEQ ID NO: 2: or
wherein the second proinsulin polypeptide comprises both P28K and K29P substitutions in an insulin B-chain of SEQ ID NO: 2: or
wherein the second proinsulin polypeptide comprises P28K, K29P, and H10D substitutions in an insulin B-chain of SEQ ID NO: 2.

8. The conjugate of claim 1, wherein the second proinsulin polypeptide comprises a signal peptide sequence, optionally wherein the signal peptide sequence is a native or engineered signal peptide sequence or wherein the signal peptide sequence is SEQ ID NO: 5.

9. The conjugate of claim 1, wherein the first proinsulin polypeptide and/or the second proinsulin polypeptide comprise an amino acid sequence selected from the group consisting of SEQ ID NOs: 8-10 or wherein the first proinsulin polypeptide and the second proinsulin polypeptide exhibit reduced activation of hormonal insulin receptor (IR) relative to native human insulin.

10. A composition comprising a conjugate of claim 1 and a pharmaceutically acceptable carrier.

11. A pharmaceutical composition comprising a pharmaceutically acceptable carrier and an effective amount of a compound of claim 1.

12. The pharmaceutical composition of claim 11, wherein the effective amount of the compound is effective to treat one or more of Type 1 diabetes, juvenile diabetes, insulin-dependent diabetes, or latent autoimmune diabetes in a subject.

13. The pharmaceutical composition of claim 12, wherein the subject is not hyperglycemic; or
wherein the subject has detectable levels of an insulin autoantibody (IAA); or
wherein the subject has detectable levels of an insulin-specific B cell population: or
wherein the subject harbors one or more human leukocyte antigen (HLA) haplotypes selected from the group consisting of: (a) DRB1*0301-DQA1*0501-DQB1*0201: (b) DRB1*0405-DQA1*0301-DQB1*0302: (c) DRB1*0401-DQA1*0301-DQB*0302; (d) DRB1*0402-DQA1*0301-DQB1*0302 (e) DRB1*0404-DQA1*0301-DQB1*0302; and (f) DRB*0801-DQB1*0401-DQB1*0402.

14. A kit comprising the conjugate of claim 1, and instructions for use.

15. A method for treating or preventing autoimmune diabetes in a subject in need thereof comprising administering to the subject an effective amount of the conjugate of claim 1.

16. The method of claim 15, wherein autoimmune diabetes comprises Type 1 diabetes, juvenile diabetes, insulin-dependent diabetes, or latent autoimmune diabetes.

17. The method of claim 15, wherein the subject has been diagnosed with or is at risk for autoimmune diabetes; or
wherein the subject is not hyperglycemic; or
wherein the subject has detectable levels of an insulin autoantibody (IAA); or
wherein the subject has detectable levels of an insulin-specific B cell population: or
wherein the subject harbors one or more human leukocyte antigen (HLA) haplotypes selected from the group consisting of: (a) DRB1*0301-DQA1*0501-DQB1*0201: (b) DRB1*0405-DQA1*0301-DQB1*0302: (c) DRB1*0401-DQA1*0301-DQB1*0302; (d) DRB1*0402-DQA1*0301-DQB1*0302 (e) DRB1*0404-DQA1*0301-DQB1*0302 and (f) DRB1*0801-DQB1*0401-DQB1*0402: or
wherein the subject is a child or adult.

18. The method of claim 15, wherein the conjugate is administered parenterally, intravenously or subcutaneously.

19. The method of claim 15, wherein administration of the conjugate induces anergy in insulin-binding B cells in the subject.

20. The method of claim 15, wherein blood glucose levels of the subject after at least one administration of the conjugate are comparable to that observed in the subject prior to the at least one administration.

* * * * *

SEQUENCE LISTING

```
<160> NUMBER OF SEQ ID NOS: 15

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 30
<212> TYPE: PRT
<213> ORGANISM: Homo sapiens
```

```
<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 35
<212> TYPE: PRT
<213> ORGANISM: Homo sapiens

<400> SEQUENCE: 3

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 4
<211> LENGTH: 21
<212> TYPE: PRT
<213> ORGANISM: Homo sapiens

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Gly Ser Ser His His His His His His Ser Ser Phe Leu Asp Pro
1               5                   10                  15

Val Leu Met

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Pro Glu Thr Gly Gly His Gly
1               5

<210> SEQ ID NO 7
<211> LENGTH: 25
<212> TYPE: PRT
<213> ORGANISM: Homo sapiens

<400> SEQUENCE: 7

Gln Val Glu Leu Gly Gly Gly Pro Gly Ala Gly Ser Leu Gln Pro Leu
1               5                   10                  15
```

```
Ala Leu Glu Gly Ser Leu Gln Lys Arg
            20              25
```

<210> SEQ ID NO 8
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Gly Ser Ser His His His His His His Ser Ser Phe Leu Asp Pro
1               5                   10                  15

Val Leu Met Phe Val Asn Gln His Leu Cys Gly Ser His Leu Val Glu
            20                  25                  30

Ala Leu Tyr Leu Val Cys Gly Glu Arg Gly Phe Phe Tyr Thr Pro Lys
        35                  40                  45

Thr Arg Arg Glu Ala Glu Asp Leu Gln Val Gly Gln Val Glu Leu Gly
    50                  55                  60

Gly Gly Pro Gly Ala Gly Ser Leu Gln Pro Leu Ala Leu Glu Gly Ser
65                  70                  75                  80

Leu Gln Lys Arg Gly Ile Val Glu Gln Cys Cys Thr Ser Ile Cys Ser
                85                  90                  95

Leu Tyr Gln Leu Glu Asn Tyr Cys Asn
            100                 105
```

<210> SEQ ID NO 9
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Gly Ser Ser His His His His His His Ser Ser Phe Leu Asp Pro
1               5                   10                  15

Val Leu Met Phe Val Asn Gln His Leu Cys Gly Ser His Leu Val Glu
            20                  25                  30

Ala Leu Tyr Leu Val Cys Gly Glu Arg Gly Phe Asp Tyr Thr Pro Lys
        35                  40                  45

Thr Arg Arg Glu Ala Glu Asp Leu Gln Val Gly Gln Val Glu Leu Gly
    50                  55                  60

Gly Gly Pro Gly Ala Gly Ser Leu Gln Pro Leu Ala Leu Glu Gly Ser
65                  70                  75                  80

Leu Gln Lys Arg Gly Ile Val Glu Gln Cys Cys Thr Ser Ile Cys Ser
                85                  90                  95

Leu Tyr Gln Leu Glu Asn Tyr Cys Asn
            100                 105
```

<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

-continued

```
Met Gly Ser Ser His His His His His Ser Ser Phe Leu Asp Pro
1               5                   10                  15

Val Leu Met Phe Val Asn Gln His Leu Cys Gly Ser His Leu Val Glu
            20                  25                  30

Ala Leu Tyr Leu Val Cys Gly Glu Arg Gly Phe Phe Tyr Thr Pro Lys
            35                  40                  45

Thr Arg Arg Glu Ala Glu Asp Leu Gln Val Gly Gln Val Glu Leu Gly
        50                  55                  60

Gly Gly Pro Gly Ala Gly Ser Leu Gln Pro Leu Ala Leu Glu Gly Ser
65                  70                  75                  80

Leu Gln Lys Arg Gly Ile Val Glu Gln Cys Cys Thr Ser Ile Cys Ser
                85                  90                  95

Leu Tyr Gln Leu Glu Asn Leu Cys Asn
            100                 105
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Leu Pro Glu Thr Gly
1               5
```

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

```
Leu Pro Glu Thr Gly Gly His His His His His His
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Leu Pro Glu Thr Gly Gly Gly
1               5
```

<210> SEQ ID NO 14
<211> LENGTH: 94
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (10)..(10)
<223> OTHER INFORMATION: H or D
<220> FEATURE:
<221> NAME/KEY: MOD_RES
<222> LOCATION: (25)..(25)
<223> OTHER INFORMATION: F or D

```
<220> FEATURE:
<221> NAME/KEY: MOD_RES
<222> LOCATION: (28)..(28)
<223> OTHER INFORMATION: P or K
<220> FEATURE:
<221> NAME/KEY: MOD_RES
<222> LOCATION: (29)..(29)
<223> OTHER INFORMATION: K or P
<220> FEATURE:
<221> NAME/KEY: MOD_RES
<222> LOCATION: (84)..(84)
<223> OTHER INFORMATION: Y or A

<400> SEQUENCE: 14

Phe Val Asn Gln His Leu Cys Gly Ser Xaa Leu Val Glu Ala Leu Tyr
1               5                  10                  15

Leu Val Cys Gly Glu Arg Gly Phe Xaa Tyr Thr Xaa Xaa Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Xaa Cys Asn Leu Pro Glu Thr Gly Gly His Gly
                85                  90

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Pro Thr Glu Gly Gly His Gly
1               5
```